US009919109B2

(12) United States Patent
Arinobe et al.

(10) Patent No.: US 9,919,109 B2
(45) Date of Patent: Mar. 20, 2018

(54) LIQUID-ADMINISTERING INSTRUMENT

(71) Applicant: TERUMO KABUSHIKI KAISHA, Tokyo (JP)

(72) Inventors: Manabu Arinobe, Hadano (JP); Masaomi Imai, Kofu (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 49 days.

(21) Appl. No.: 15/067,811

(22) Filed: Mar. 11, 2016

(65) Prior Publication Data

US 2016/0206830 A1    Jul. 21, 2016

Related U.S. Application Data

(63) Continuation of application No. PCT/JP2014/073576, filed on Sep. 5, 2014.

(30) Foreign Application Priority Data

Sep. 13, 2013    (JP) .................. 2013-191205

(51) Int. Cl.
*A61M 5/32* (2006.01)
*A61M 5/24* (2006.01)
*A61M 5/315* (2006.01)
*A61M 5/20* (2006.01)

(52) U.S. Cl.
CPC ........ *A61M 5/3202* (2013.01); *A61M 5/2033* (2013.01); *A61M 5/24* (2013.01); *A61M 5/31543* (2013.01); *A61M 2005/006* (2013.01); *A61M 2005/2073* (2013.01)

(58) Field of Classification Search
CPC .............. A61M 5/3202; A61M 5/2033; A61M 2005/206; A61M 5/326
USPC .................................. 604/192–198
See application file for complete search history.

(56) References Cited

U.S. PATENT DOCUMENTS 6,569,123 B2 * 5/2003 Alchas ................... A61M 5/46
604/192

* cited by examiner

*Primary Examiner* — Phillip Gray
(74) *Attorney, Agent, or Firm* — Foley & Lardner LLP

(57) ABSTRACT

A liquid administration tool includes a structure including a tubular body in which liquid is fillable, the tubular body having a bottom portion at a distal end and, an opening portion at a proximal end, and a needle tube positioned at a distal portion of the tubular body, the needle tube having a needle tip at a distal end thereof, and the needle tube being communicable at a proximal end thereof with an inside of the tubular body; an operation member having a pusher; a cover member; a biasing member configured to bias the cover member in the distal direction; a locking unit configured to restrict the movement of the cover member; and a movement amount restriction unit configured to restrict the movement amount of the cover member.

7 Claims, 33 Drawing Sheets

LIQUID-ADMINISTERING INSTRUMENT

CROSS-REFERENCE TO RELATED APPLICATIONS

This application is a continuation application filed under 35 U.S.C. 111(a) claiming the benefit under 35 U.S.C. §§ 120 and 365(c) of PCT International Application No. PCT/JP2014/073576, filed on Sep. 5, 2014, which claims priority to Japanese Patent Application No. 2013-191205, filed on Sep. 13, 2013. The contents of these applications are hereby incorporated by reference in their entireties.

BACKGROUND

The present disclosure relates to a liquid administration instrument.

An injection device used when drug solution is administrated is known (for example, refer to Japanese Patent No. 4176631). The injection device disclosed in Japanese Patent No. 4176631 includes a main body portion which has a cylindrical shape and in which drug solution is filled aseptically, a needle tube fixed to a distal portion of the main body portion, a gasket (stopper) capable of slidably moving in the inside of the main body portion, a plunger configured to engage with a proximal side of the gasket and press the gasket in a direction toward the distal end to discharge drug solution from the needle tube, and a cover member (shield) capable of covering the needle tube. When drug solution is administrated using an injection device having such a configuration, the needle tube punctures a living body in a state in which the cover member is moved backwards until the needle tube is exposed, and then the plunger is operated and pressed as it is. Consequently, the drug solution is discharged from a aperture by the gasket and can be administrated into the living body through the needle tube. After the administration of the drug solution is performed, if the needle tube is pulled out from the living body and the cover member is moved forwards, then the needle tube is covered with the cover member to allow the injection device to be discarded safely. It is to be noted that the injection device disclosed in Japanese Patent No. 4176631 is configured such that, if the needle tube is covered by forward movement of the cover member, then the cover member is prevented from being moved backwards again. Consequently, the state in which the needle tube is covered with the cover member after the administration can be maintained with certainty.

SUMMARY

However, when drug solution is being administrated into the living body, in order to moderate pain caused by drug solution or the like, it is sometimes desired to pull off a needle tube from the living body to temporarily interrupt administration. In this case, if the cover member is moved forwards once to cover the needle tube, then the cover member is placed into a state in which the cover member is blocked from moving backwards again as described hereinabove. Therefore, the needle tip cannot be exposed. As a result, there is a problem that administration cannot be re-started and administration of drug solution of a predetermined amount cannot be performed.

One object of certain embodiments of the present disclosure is to provide a liquid administration tool which can re-start administration even if, when administration of drug solution is performed, a needle tube is pulled out once from a living body to interrupt administration of the drug solution.

This object can be achieved by the following.

According to one embodiment, there is provided a liquid administration tool including a structure including a tubular body which has a bottom portion at a distal portion and an opening portion at a proximal portion and in which liquid can be filled and a needle tube which is positioned at a distal portion of the tubular body and has an incisive needle tip at a distal end thereof, the needle tube being communicable at a proximal end thereof with the inside of the tubular body, an operation member having a pusher and configured to perform a pressing operation of moving the pusher in a direction toward the distal end to discharge the liquid from the needle tube, a cover member movable between a predetermined first position at which the cover member covers at least the needle tip of the needle tube and a predetermined second position at which the cover member is retracted in a direction toward the proximal end from the predetermined first position and the needle tip is exposed, a biasing member configured to bias the cover member in the direction toward the distal end, a locking unit configured to restrict, when the cover member is moved from the predetermined second position to the predetermined first position by biasing force of the biasing member and a movement amount of the cover member reaches a lock permitting movement amount, the movement of the cover member to the predetermined second position, and a movement amount restriction unit configured to restrict the movement amount of the cover member such that the movement amount when the cover member is moved in the direction toward the distal end by the biasing force of the biasing member does not reach the lock permitting movement amount until the cover member is positioned at the predetermined second position and the pressing operation is completed.

In the liquid administration tool described above, the cover member may include a cover main body having a tubular shape, and a rotor provided on the cover main body for relative rotation around a center axis of the cover main body and configured to rotate in an interlocking relationship with the pressing operation.

In the liquid administration tool described above, the movement amount restriction unit may include a projection provided on the rotor, and an engaging portion provided on the operation member and engageable with the projection.

In the liquid administration tool described above, the operation member may have a grasping portion having a cylindrical shape and set to an outer periphery side of the structure and the rotor being grasped upon use of the liquid administration tool, and the engaging portion may be provided on an inner circumferential face of the grasping portion.

In the liquid administration tool described above, the movement amount restriction unit may have an attachment face provided on the operation member and configured to attach, upon the pressing operation, to the projection to rotate the rotor.

In the liquid administration tool described above, the attachment face may be provided on the pusher.

In the liquid administration tool described above, the operation member may have an attachment portion configured to attach to the projection if the movement amount of the cover member reaches the lock permitting movement amount after the pressing operation is completed, and a position in the direction toward the distal end of the cover member with respect to the operation member may be restricted by attachment of the projection to the attachment portion.

In the liquid administration tool described above, the liquid may be drug solution.

According to the present disclosure, preferably the liquid administration tool is configured such that the movement amount restriction unit blocks the movement of the cover member in the direction toward the distal end, and in the state in which the movement amount restriction unit blocks the movement of the cover member in the direction toward the distal end, at least the needle tip of the needle tube is covered with the cover member.

Alternatively, the liquid administration tool may be configured such that the movement amount restriction unit blocks the movement of the cover member in the direction toward the distal end, and in the state in which the movement amount restriction unit blocks the movement of the cover member in the direction toward the distal end, the needle tip of the needle tube is exposed from the cover member.

Preferably, the liquid administration tool is configured such that the cover member includes a cover main body having a tubular shape, and a rotor provided on the cover main body and configured for relative rotation around a center axis of the cover main body and for relative movement in a direction of the center axis. Further, the liquid administration tool presses, when the liquid is to be administrated into the living body, the cover main body against the surface of the living body, and if the pressing of the cover main body against the surface of the cover main body is cancelled before the pressing operation is completed, then while the movement amount of the cover member is restricted by the movement amount restriction unit, the cover member is moved in the direction toward the distal end with respect to the rotor by the biasing force of the biasing member until at least the needle tip of the needle tube is covered with the cover member.

Preferably, the liquid administration tool is configured such that, immediately before the pressing operation is completed, the rotor is interlocked with the pressing operation to rotate with respect to the cover main body and the operation member.

Preferably, the liquid administration tool is configured such that the movement amount restriction unit includes a first projection provided on the rotor, and an engaging portion provided on the operation member and engageable with the first projection.

Preferably, the liquid administration tool is configured such that the operation member has a grasping portion having a tubular shape and set on an outer circumferential side of the structure and the rotor, the grasping portion being configured to be grasped upon use of the liquid administration tool, and the engaging portion is provided on an inner circumferential face of the grasping portion.

Preferably, the liquid administration tool is configured such that the movement amount restriction unit includes a second projection provided on the rotor, and an attachment face configured to attach, upon the pressing operation, to the second projection to rotate the rotor.

Preferably, the liquid administration tool is configured such that the operation member has a grasping portion having a tubular shape and set on an outer circumferential side of the structure and the rotor, the grasping portion being configured to be grasped upon use of the liquid administration tool, and the attachment face is provided on an inner circumferential face of the grasping portion.

Preferably, the liquid administration tool is configured such that the operation member has an attachment portion configured to attach to the first projection when the movement amount of the cover member reaches the lock permitting movement amount after the pressing operation is completed, and the first projection is attached to the attachment portion to restrict the position of the cover member in the direction toward the distal end with respect to the operation member.

Preferably, the liquid administration tool is configured such that it includes a pair of engaging portions, and a pair of first projections. Further the liquid administration tool is configured such that each of the engaging portions has a region in which the distance of the engaging portion in the axial direction from the proximal end of the operation member gradually decreases stepwise in a direction of rotation of the rotor, and that the distance of the region in which the distance of one of the engaging portions from the proximal end of the operation member gradually decreases stepwise and the distance of the region of the other one of the engaging portions from the proximal end of the operation member gradually decreases stepwise are different from each other.

Preferably, the liquid administration tool is configured such that at least one of the regions of the engaging portions in which the distance gradually decreases stepwise and the first projections has an inclined face inclined with respect to the direction of rotation of the rotor.

Preferably, the liquid administration tool is configured such that the engaging portions have a region in which the distance in the axial direction from the proximal end of the operation member gradually decreases stepwise in the direction of rotation of the rotor.

Preferably, the liquid administration tool is configured such that the region of the engaging portions in which the distance gradually decreases stepwise has an inclined face inclined with respect to the direction of rotation of the rotor.

Preferably, the liquid administration tool is configured such that the tubular body has an inner tube into which the liquid can be filled, and an outer tube disposed concentrically with the inner tube on an outer periphery side of the inner tube and disposed for rotation around a center axis of the inner tube relative to the inner tube.

When administration of liquid is performed, for example, pain by the liquid or puncture pain by a needle tube sometimes occurs, by which it is obliged to pull out the needle tube once from the living body to interrupt the administration of liquid. In this case, the cover member moves in the direction toward the distal end back to the predetermined first position by the biasing force of the biasing member, and if the movement amount of the cover member reaches the lock permitting movement amount, then the movement of the cover member to the predetermined second position is restricted by the locking unit. However, since the movement amount restriction unit restricts the amount of movement of the cover member, establishment of such a situation as just described can be prevented with certainty. Then, after the pain disappears, the needle tube can puncture the living body again to re-start the pressing operation.

In this manner, with the liquid administration tool of the present disclosure, when administration of liquid is performed, even if the administration of liquid is interrupted, the administration can be re-started with certainty before the administration of liquid is completed. Consequently, desired administration of liquid can be performed with certainty.

Further, after the administration of liquid is completed, the movement of the cover member to the predetermined second position is restricted by the locking unit. Consequently, the state in which the needle tip of the needle tube is covered with the cover member is maintained, and as a result, puncture in error by the needle tip of the needle tube after use can be prevented with certainty.

DETAILED DESCRIPTION

In the following, a liquid administration tool of the present disclosure is described in detail according to the suitable embodiments with reference to the accompanying drawings.

First Embodiment

First, a liquid administration tool according to a first embodiment is described below with reference to FIGS. 1 to 29.

Note that, in the following description, the upper side in FIGS. 1 to 29 is referred to as "proximal end (rear end)" or "top (upper)," the lower side as "distal end" or "bottom (lower)," and an upward and downward direction as "axial direction" or "longitudinal direction" (this similarly applies to the figures for the second and following embodiments).

Figure 1:
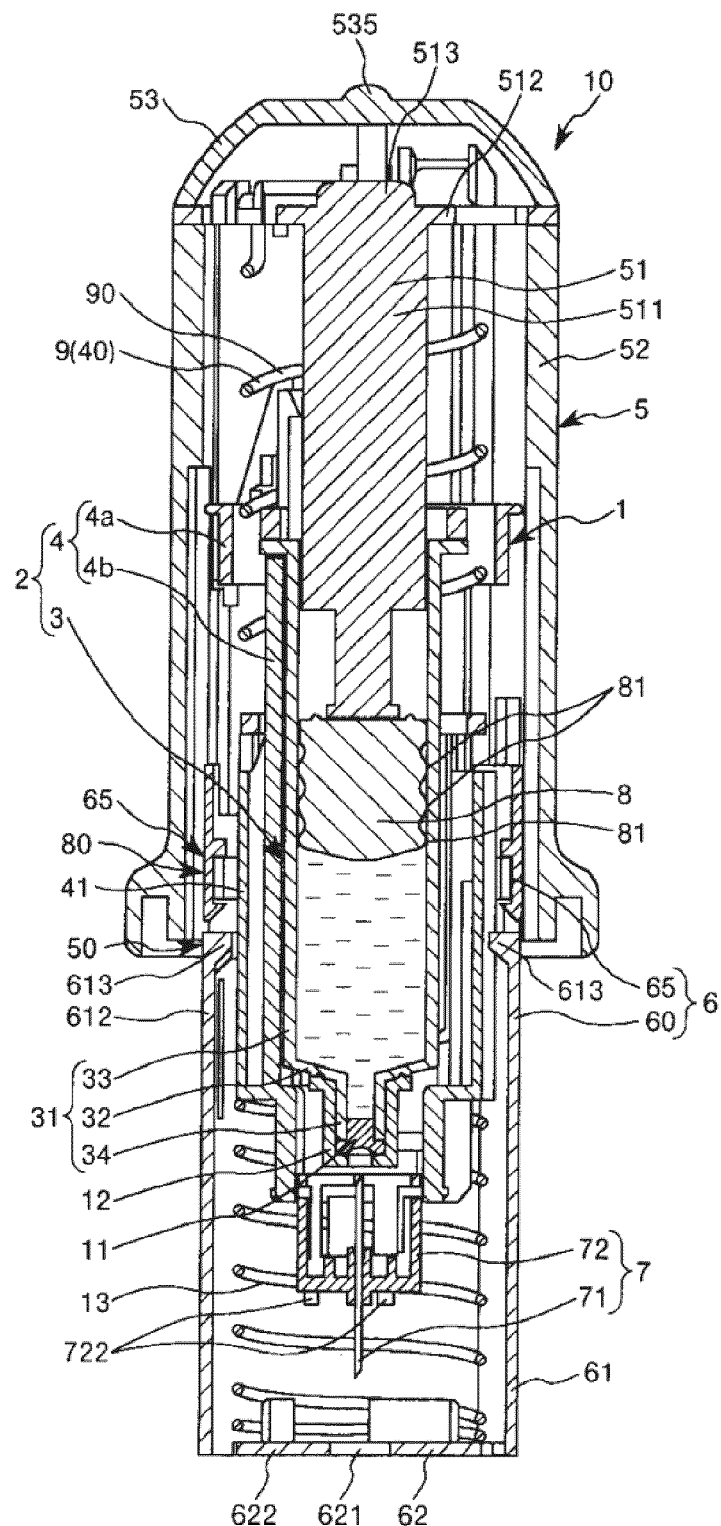
FIG. 1 is a vertical sectional view depicting a first embodiment of a liquid administration tool of the present disclosure.
Figure 2:
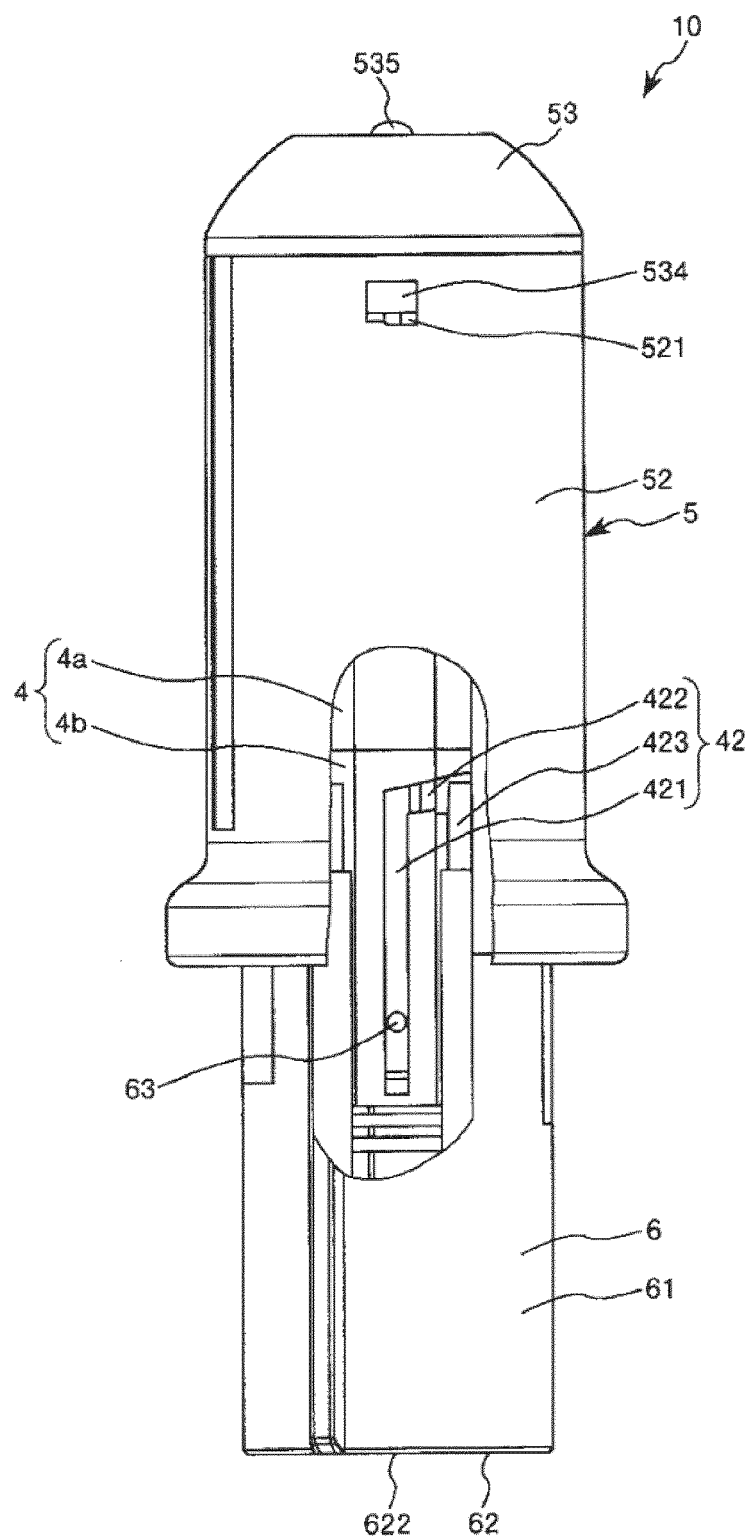
FIG. 2 is a lateral view of the liquid administration tool depicted in FIG. 1.
Figure 3:
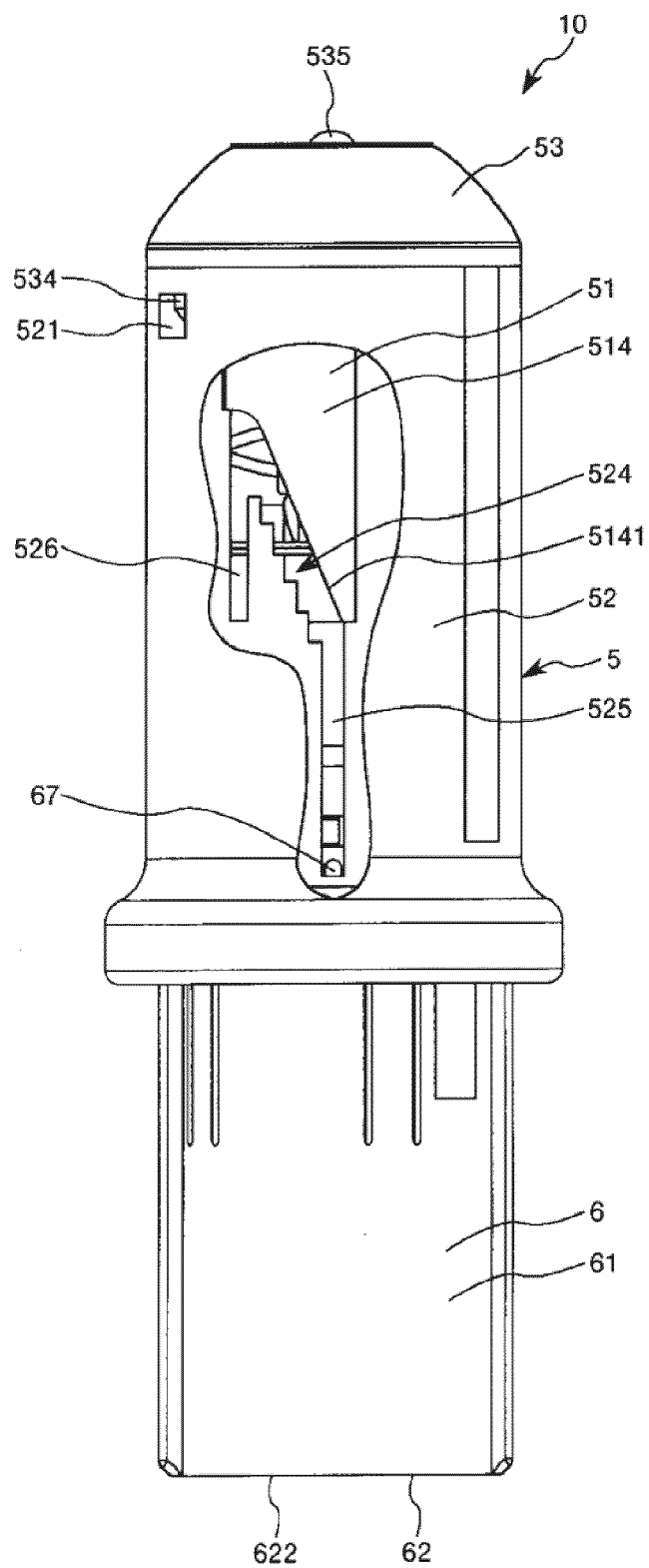
FIG. 3 is a lateral view of the liquid administration tool depicted in FIG. 1.

A liquid administration tool 10 depicted in FIGS. 1 to 3 is a medical device used when liquid is administrated (injected) into a living body. Note that, while the liquid is selected suitably in accordance with an object of use, drug solution to be used mainly for dermenchysis such as, for example, hematinic, vaccine, hormone preparation, anti-rheumatic, anti-cancer agent, anesthetic, blood coagulation inhibitor, or gel formulation is available as the liquid.

The liquid administration tool 10 includes an inner side structure body (structure) 1, a gasket 8, an operation member 5, a cover member 6, a coil spring 13, an auxiliary unit 40, a locking unit 50, and a movement amount restriction unit 80. The cover member 6 is disposed on the outer periphery side of the inner side structure body 1. The coil spring 13 is a biasing member for biasing the cover member 6 in the direction toward the distal end.

As depicted in FIG. 1, the inner side structure body 1 includes a tubular body 2 configured from an inner tube 3 and an outer tube 4, a puncture needle 7 configured from a double-ended needle (needle tube) 71 and a supporting member 72, and the gasket 8 provided in the inner tube 3 (tubular body 2) and slidably movable in an axial direction of the inner tube 3. The supporting member 72 may not necessarily be provided but a needle syringe may be provided.

As depicted in FIG. 1, the inner tube 3 has an inner tube main body 31. The inner tube main body 31 is configured from a bottom portion 32 at a distal portion thereof, a side wall 33 provided uprightly from an edge portion of the bottom portion 32, and a member having an opening portion at a proximal portion thereof, namely, a member having a bottomed tubular shape. Further, liquid can be filled into the inside of the inner tube 3. Further, an aperture 34 is formed integrally in a projecting manner at the distal portion of the inner tube main body 31, namely, at a central portion of the bottom portion 32. The aperture 34 has a diameter reduced from that of the side wall 33 of the inner tube main body 31, and liquid passes through the aperture 34 such that it is taken in or discharged from the aperture 34.

Further, the inner tube 3 has a sealing member (sealing portion) 11 for sealing the aperture 34 of the inner tube main body 31 in a liquid tight state, and a fixing member 12 for fixing the sealing member 11 from the distal side thereof.

The sealing member 11 is configured from an elastic body and has a projection portion formed on the proximal surface thereof, and the aperture 34 is sealed in a liquid tight state by fitting the projection portion in the aperture 34 in a liquid tight state.

The fixing member 12 is a tubular member. The fixing member 12 is fitted from the outer periphery side of the sealing member 11 and the aperture 34 to fix the sealing member 11 to the inner tube main body 31. Consequently, separation of the sealing member 11 from the inner tube main body 31 is prevented with certainty. Note that, as a fixing method for the fixing member 12, a method by adhesion, another method by welding or the like may be available.

Further, the constituent materials for the inner tube main body 31, the fixing member 12, the outer tube 4, the cover member 6, the supporting member 72, and the operation member 5 are not limited particularly, and various kinds of resin such as, for example, polyester such as polyvinyl chloride, polyethylene, polypropylene, cyclic polyolefin, polystyrene, poly (4-methylpentene-1), polycarbonate, acrylic resin, acrylonitrile-butadiene-styrene copolymer, polyethylene terephthalate, polyethylene naphthalate or the like, butadiene-styrene copolymer, or polyamide (for example, nylon 6, nylon 6.6, nylon 6.10, or nylon 12) are available. It is preferable to use resin such as polypropylene, cyclic polyolefin, polyester, or poly (4-methylpentene-1) from among various kinds of resin just described in that molding is performed easily.

Further, the elastic materials for configuring the sealing member 11 and the gasket 8 are not limited particularly, and elastic materials such as, for example, various rubber materials such as natural rubber, butyl rubber, isoprene rubber, butadiene rubber, styrene-butadiene rubber, or silicone rubber, various kinds of thermoplastic elastomers such as polyurethane-based, polyester-based, polyamide-based, olefin-based, or styrene-based elastomer, or mixtures of the materials just described are available.

The outer tube 4 is disposed concentrically with the inner tube 3 on the outer periphery side of the inner tube 3. As depicted in FIGS. 1 and 10 to 14, the outer tube 4 has a generally tubular shape which is open the opposite ends thereof and has a length greater than that of the inner tube 3. Further, the outer tube 4 can be provided for rotary movement around the axis of the inner tube 3.

Figure 10:
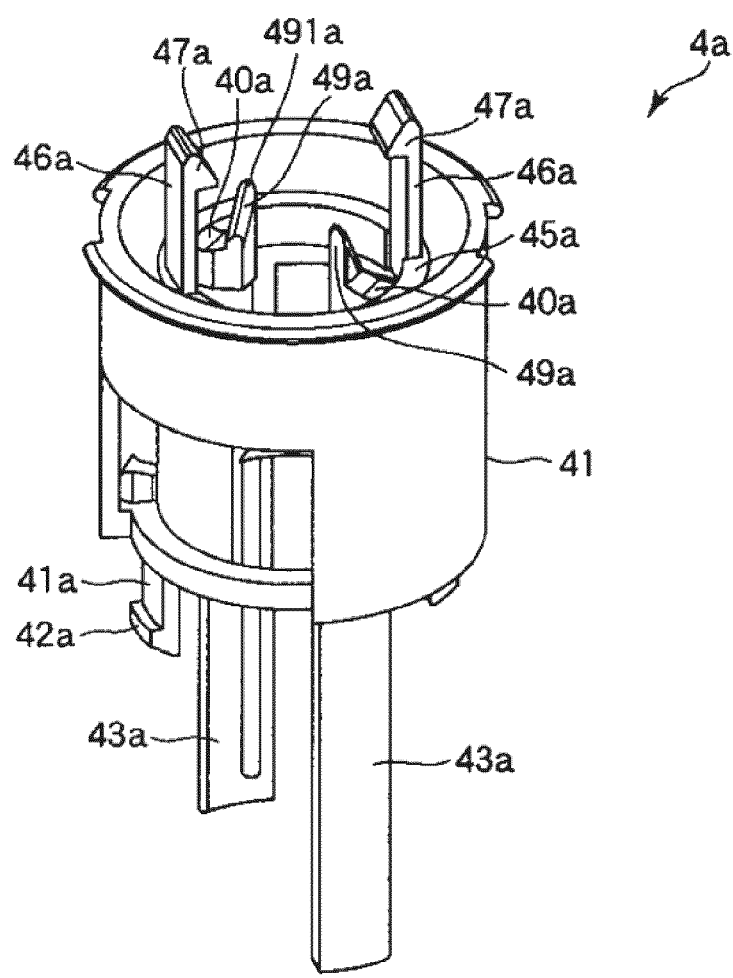
FIG. 10 is a perspective view of a proximal side member of an outer tube of the liquid administration tool depicted in FIG. 1.
Figure 12:
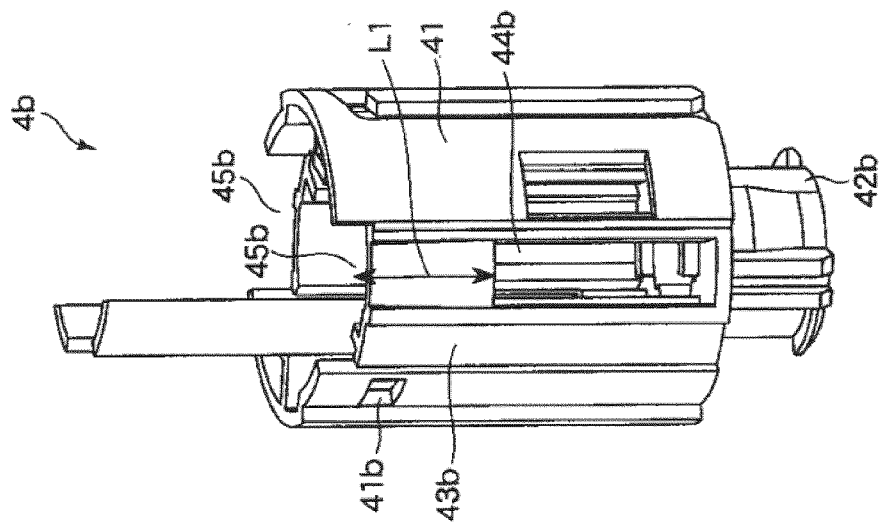
FIG. 12 is a perspective view of a distal side member of the outer tube of the liquid administration tool depicted in FIG. 1.
Figure 11:
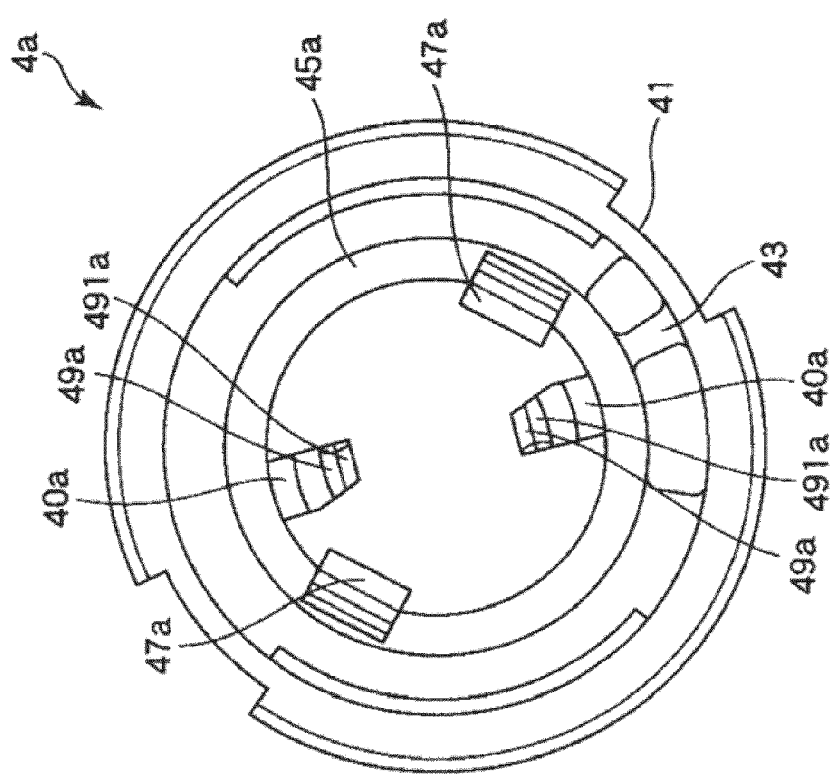
FIG. 11 is a top plan view of the proximal side member of the outer tube of the liquid administration tool depicted in FIG. 1.
Figure 14:
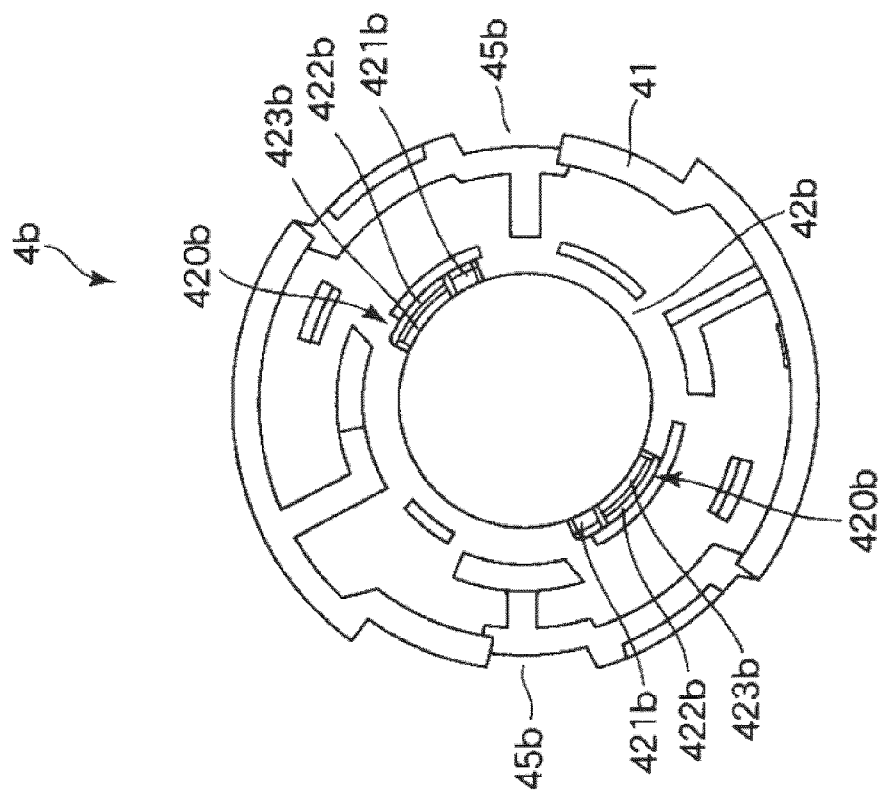
FIG. 14 is a top plan view of the distal side member of the outer tube of the liquid administration tool depicted in FIG. 1.
Figure 13:
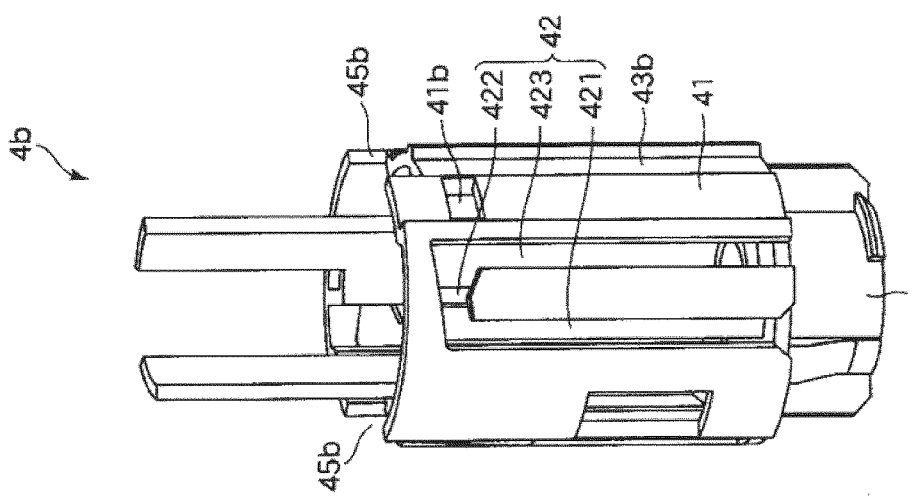
FIG. 13 is a perspective view of the distal side member of the outer tube of the liquid administration tool depicted in FIG. 1.

The outer tube 4 is configured from a proximal side member 4a disposed on the proximal side and depicted in FIGS. 10 and 11 and a distal side member 4b disposed on the distal side and depicted in FIGS. 12 to 14. A pair of hole portions 41b are formed on the proximal side of the distal side member 4b such that they are disposed in an opposing relationship to each other. Further, a pair of arm portions 41a having elasticity are formed in a projecting manner in a direction toward the distal end on the distal side of the proximal side member 4a such that they are disposed in an opposing relationship to each other. Each of the arm portions 41a has a pawl 42a formed at a distal portion thereof such that it projects to the outer side. The pawls 42a are inserted from the inner side of the proximal side of the distal side member 4b into and engaged with the hole portions 41b thereby to interlock the proximal side member 4a and the distal side member 4b to each other.

Note that the method for interlocking the proximal side member 4a and the distal side member 4b to each other is not limited to this, and fusion such as, for example, adhesion thermal fusion by adhesive, solvent or the like, high-frequency fusion, supersonic fusion or the like is available.

Further, the outer tube 4 has a body portion 41, a reduced diameter portion 42b, and another reduced diameter portion 45a. The reduced diameter portion 42b is formed at the distal side of the body portion 41 and has a diameter reduced from that of the body portion 41. The reduced diameter portion 45a is formed at a proximal portion of the body portion 41 and has a diameter reduced from that of the body portion 41.

A pair of groove groups 420b are formed at an inner peripheral portion of the reduced diameter portion 42b and disposed in an opposing relationship to each other (refer to FIG. 14). Note that, since the groove groups 42b are similar to each other, one of the groove groups 42b is described below as representative.

The groove group 420b has a vertical groove 421b extending in the axial direction of the reduced diameter portion 42b and formed linearly, a horizontal groove 422b communicated with the vertical groove 421b, and another horizontal groove 423b disposed on the proximal side of the horizontal groove 422b. The horizontal grooves 422b and 423b are formed along a circumferential direction of the reduced diameter portion 42b. Further, the horizontal groove 422b is communicated at one end portion thereof with a proximal portion of the vertical groove 421b. Note that, while the reduced diameter portion 45a is formed in the present embodiment, the reduced diameter portion 45a may not be formed.

Further, a pair of grooves 43b and a pair of elongated holes 44b which extend through the body portion 41 are provided on the body portion 41 of the distal side member 4b. The grooves 43b are disposed in an opposing relationship to each other and, similarly, also the elongated holes 44b are disposed in an opposing relationship to each other. It is to be noted, since the grooves 43b have shapes same as each other, one of the grooves 43b is described below as a representative. Similarly, since also the elongated holes 44b have shapes same as each other, one of the elongated holes 44b is described below as a representative. Note that, while the groove 43b in the present embodiment has a bottom, the groove 43b may be configured so as to extend the body portion 41. The same effects are achieved also in this case (not depicted). Further, while the elongated hole 44b in the present embodiment extends through the body portion 41, the elongated hole 44b may be depressed without extending through the body portion 41. In this case, the same effects are achieved as well (not depicted).

Further, the groove 43b and the elongated hole 44b are provided in a juxtaposed relationship with each other in a circumferential direction of the body portion 41. Note that, in the present embodiment, the groove 43b is disposed on the left side of the elongated hole 44b.

Further, the groove 43b and the elongated hole 44b extend along the axis of the body portion 41. Further, the groove 43b is formed from the distal end to the proximal end of the distal side member 4b and is open to the distal end and the proximal end of the distal side member 4b. Further, an end face on the proximal side of the elongated hole 44b is positioned on the distal side with respect to the proximal end of the groove 43b and is set perpendicularly to the axis of the body portion 41.

Further, a space 45b is formed at a location on the proximal side of the groove 43b and the elongated hole 44b in the body portion 41.

Further, a portion of the body portion 41 between the elongated hole 44b and the space 45b has a thickness gradually decreasing from the distal side to the proximal side, and a tapering face is formed on an outer circumferential face of the body portion 41. Consequently, the projection 613 of the cover member 6 can smoothly move from the space 45b to the elongated hole 44b.

Further, a pair of projecting portions 40a are formed on the proximal side of the reduced diameter portion 45a of the proximal side member 4a such that they are disposed in an opposing relationship to each other. The projecting portions 40a are formed so as to project from the inner circumferential face of the reduced diameter portion 45a toward the inner side, namely, toward the center axis.

Further, a projection (second engaging portion) 49a is formed at an end portion (distal portion) of each of the projecting portions 40a on the center axis side such that it projects in a direction toward the proximal end.

Each of the projections 49a has, as a rotary unit, an inclined face 491a to which step portions 516 hereinafter described are attached. The rotary unit rotates a step portion 516 and the projection 49a, which are in an engaged state with each other, relatively around the center axis of the inner side structure body 1 to establish a disengaged state between them. The inclined face 491a is, in the configuration depicted, a flat face. The inclined face 491a is directed in a tangential direction to a circle centered at the center axis of the inner side structure body 1 and passing the inclined face 491a as viewed in plan. Consequently, when the step portions 516 move along the inclined face 491a relative to the projection 49a, the outer tube 4 rotates around the center axis thereof relatively to the operation member 5.

Further, an inclination angle θ of the inclined face 491a is not limited particularly and is set suitably in accordance with various conditions. However, the inclination angle θ preferably is 5 degrees to 85 degrees, and more preferably is 20 degrees to 70 degrees.

Note that the shape of the inclined face 491a is not limited to a planar shape and may be a curved face. Further, the number of inclined faces 491a and the projecting portions 40a is not limited to two but may be, for example, one or three or more. Further, a flattened face may be used in place of the inclined face 491a.

Further, a pair of arm portions 46a having elasticity are formed in a projecting manner in a direction toward the proximal end on the proximal side of the reduced diameter portion 45a of the proximal side member 4a such that they are disposed in an opposing relationship to each other. A pawl 47a is formed at a distal portion of each of the arm portions 46a and projects toward the inner side.

Further, a pair of projecting pieces 43a are formed in a projecting manner in a direction toward the distal end on the distal side of the proximal side member 4a such that they are disposed in an opposing relationship to each other. Each of the projecting pieces 43a functions, in a state after use (in a state when administration is completed), as an index indicating that the administration of liquid is completed.

Further, the inner tube 3 is installed between the projecting portions 40a and the reduced diameter portion 42b of the outer tube 4 such that it is sandwiched by the proximal side member 4a and the distal side member 4b from above and below thereby to prevent movement of the inner tube 3 in the axial direction with respect to the outer tube 4.

Further, a pair of cam grooves 42 are formed on an outer circumferential face of the body portion 41 of the outer tube 4 such that a pair of projections 63 hereinafter described of the cover member 6 are inserted into the cam grooves 42. While, in the present embodiment, the cam grooves 42 are formed such that they extend through the wall portion of the body portion 41, the present disclosure is not limited to this, and they need not extend through the wall portion of the body portion 41. It is to be noted that, since the cam grooves 42 are similar to each other, in the following description, one of the cam grooves 42 is described as a representative.

The cam groove 42 is configured from a linear groove (second groove) 421, an inclined groove (first groove) 422, and another linear groove (third groove) 423 provided on an outer circumferential face of the body portion 41. The linear groove 421 extends in the axial direction of the outer tube 4 and is formed linearly. The inclined groove 422 is formed in an inclined relationship by a predetermined angle with respect to the axial line of the outer tube 4. The linear groove 423 extends in the axial direction of the outer tube 4 and is formed linearly. A distal portion of the linear groove 423 is positioned on the proximal side with respect to the distal portion of the linear groove 421, and a proximal portion of the linear groove 423 is positioned on the proximal side with respect to the proximal portion of the linear groove 421. Further, the inclined groove 422 is formed shorter than one round of the body portion 41.

The linear groove 421, the inclined groove 422, and the linear groove 423 are formed continuously from the left side toward the right side in FIGS. 2 and 13. Further, the proximal portion of the linear groove 421 and the distal portion of the inclined groove 422 (end portion on the left side in FIGS. 2 and 13) are communicated with each other. Further, the proximal portion of the inclined groove 422 (end portion on the right side in FIGS. 2 and 13) and the proximal portion of the linear groove 423 are communicated with each other.

If the cover member 6 is moved in the axial direction of the outer tube 4 by the cam groove 42 and the projection 63 of the cover member 6, then the outer tube 4 rotates by a predetermined angle to the right side in FIG. 1 with respect to the cover member 6 and the inner tube 3. In particular, since the projection 63 moves relative to the cover member 6 along the inclined groove 422, the outer tube 4 rotates around the center axis relative to the cover member 6. Consequently, the outer tube 4 rotates around the center axis of the outer tube 4 relative to the operation member 5. Accordingly, the rotary unit is configured from the projection 63 and the inclined groove 422.

Further, when the cover member 6 is positioned at a position (A) hereinafter described, the projection 63 is inserted in the linear groove 421. Consequently, the outer tube 4 is prevented from rotating around the center axis relative to the cover member 6, and therefore, the outer tube 4 is prevented from rotating relative to the operation member 5. Accordingly, the projection 63 and the linear groove 421 configure a rotation preventing unit for preventing, in an engaged state thereof, relative rotation of the inner side structure body 1, which is configured from the step portion (first engaging portion) 516 and the projection (second engaging portion) 49a, around the center axis.

Note that the grooves may be provided on the cover member 6 while the protrusions are provided on the outer tube 4.

As depicted in FIG. 1, the puncture needle 7 is disposed at the distal portion of the tubular body 2. The puncture needle 7 is configured from the double-ended needle 71 and the supporting member 72 for supporting and fixing the double-ended needle 71.

The double-ended needle 71 is a hollow needle tube, and has an incisive distal side needle tip at the distal end thereof and has an incisive proximal side needle tip at the proximal end thereof as well. The double-ended needle 71 can puncture a living body with the distal side needle tip thereof and can puncture the sealing member 11 of the inner tube 3 with the proximal side needle tip thereof.

The lumen portion (hollow portion) of the double-ended needle 71 is communicated with the inner tube 3 in a state in which the proximal side needle tip punctures the sealing member 11 of the inner tube 3 and functions as a flow path along which liquid flows from the inner tube 3.

After the distal side needle tip of the double-ended needle 71 punctures a living body to a predetermined depth from the skin, the proximal side needle tip of the double-ended needle 71 punctures the sealing member 11 of the inner tube 3. Then, liquid is injected through the flow path of the double-ended needle 71 into the body.

Note that the constituent material of the double-ended needle 71 is not limited particularly, and, for example, such metal materials as stainless steel, aluminum or aluminum alloys, or titanium or titanium alloys can be applied.

The double-ended needle 71 having such a configuration as described above is mounted at a distal portion of the outer tube 4 (tubular body 2), namely, at the reduced diameter portion 42b, for movement along an axial direction of the outer tube 4 through the supporting member 72. The supporting member 72 supports the double-ended needle 71 for movement along the axial direction with respect to the outer tube 4. The supporting member 72 has a bottomed tubular shape. The double-ended needle 71 is supported and fixed at an intermediate portion thereof by and to a bottom portion of the supporting member 72.

Figure 18:
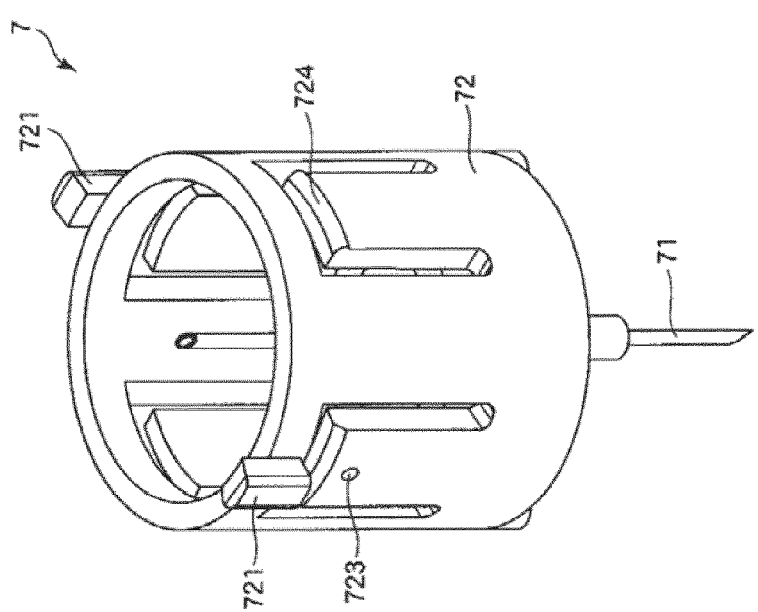
FIG. 18 is a perspective view of a puncture needle of the liquid administration tool depicted in FIG. 1.

Further, two projections 721 are formed in an opposing relationship to each other on an outer circumferential face of a proximal portion of the supporting member 72 (refer to FIG. 18). A protrusion 723 is formed on the distal side of each of the projections 721 on the outer circumferential face of the supporting member 72.

In an unused state (initial state), the projections 721 are inserted in the vertical grooves 421b of the reduced diameter portion 42b of the distal side member 4b of the outer tube 4. The projections 721 are engaged with a distal portion of the vertical grooves 421b to prevent the puncture needle 7 from being separated from the distal portion of the tubular body 2.

The projections 721 are engaged with the vertical grooves 421b to prevent rotary movement of the puncture needle 7 in a circumferential direction. This can prevent coring when the proximal side needle tip of the double-ended needle 71 penetrates the sealing member 11.

Two ribs 724 are formed in an opposing relationship to each other on an outer circumferential face of a proximal portion of the supporting member 72 (refer to FIG. 18). The ribs 724 extend along a circumferential direction of the supporting member 72 and are individually disposed between the two projections 721 in the circumferential direction of the supporting member 72. The ribs 724 are attached to an inner circumferential face of the reduced diameter portion 42b of the distal side member 4b of the outer tube 4 so that the puncture needle 7 can be prevented from rattling with respect to the outer tube 4.

Further, four projections 722 are provided in an juxtaposed relationship at equal angular intervals in a circumferential direction of the supporting member 72 on a distal surface of the supporting member 72 such that they project in a direction toward the distal end (refer to FIG. 1).

As described hereinabove, the puncture needle 7 is supported on the outer tube 4 for movement along an axial direction of the outer tube 4 through the supporting member 72. Consequently, the puncture needle 7 can assume a spaced state depicted in FIG. 1 in which the proximal side needle tip of the double-ended needle 71 is spaced from the sealing member 11 of the tubular body 2 and a puncture state depicted in FIGS. 19 and 22 in which the proximal side needle tip of the double-ended needle 71 punctures the sealing member 11. Therefore, unintended leakage of liquid from the double-ended needle 71 is prevented until the puncture state is established.

As depicted in FIG. 1, the cover member 6 is disposed on an outer circumference side of the outer tube 4 (tubular body 2).

The cover member 6 is supported for movement in an axial direction with respect to the outer tube 4 (tubular body 2) similarly to the puncture needle 7. Consequently, after the cover member 6 is brought into contact at a distal surface 622 thereof with a living body, the distal side needle tip of the double-ended needle 71 punctures the living body to a predetermined depth from the skin.

The cover member 6 assumes five stages (positions) as hereinafter described after use thereof is started until the use is ended. The five positions include a first position (position (A)) (refer to FIGS. 1 to 3), a second position, a third position (refer to FIG. 20), a fourth position (refer to FIG. 23), and a fifth position (position (A)) (refer to FIG. 26). The first position is a position before use, and at the first position, the cover member 6 projects to the distal side from the distal side needle tip of the double-ended needle 71. At the second position, the cover member 6 is retracted in the direction toward the proximal side from the first position but before the outer tube 4 rotates with respect to the cover member 6 and the inner tube 3. The third position is a position after the outer tube 4 is rotated by a predetermined angle with respect to the cover member 6 and the inner tube 3. The fourth position is a position when the distal portion of the operation member 5 reaches the distal portion of the cover member 6 and the administration is completed. The fifth position is a position after the cover member 6 moves in the direction toward the distal end from the fourth position (third position) and the cover member 6 projects to the distal side from the distal side needle tip of the double-ended needle 71 and then the safety unit after the completion of the administration is rendered operative.

Note that, in the present embodiment, when the cover member 6 is positioned at the first position, the distal surface 622 of the cover member 6 projects to the distal side from the distal side needle tip of the double-ended needle 71 and the distal side needle tip of the double-ended needle 71 is covered with the cover member 6. Consequently, since the distal side needle tip of the double-ended needle 71 is not exposed until the cover member 6 moves from the first position to the proximal side, it can be prevented that the user pierces the user itself with the distal side needle tip of the double-ended needle 71 in error before puncture and that the distal side needle tip of the double-ended needle 71 is damaged. Further, when the cover member 6 is positioned at a position from the second position to the fourth position (position (B)), the distal side needle tip of the double-ended needle 71 is exposed from the distal end of the cover member 6.

Note that, when the cover member 6 is at the first position, the aforementioned puncture needle 7 is in a spaced state in which it is positioned on the proximal side with respect to the distal portion of the cover member 6. On the other hand, when the cover member 6 moves to the second position, the cover member 6 pushes the double-ended needle 71 to move in the direction toward the proximal end (double-ended needle 71 to move together with the supporting member 72), whereupon the proximal side needle tip of the double-ended needle 71 pierces the sealing member 11 of the tubular body 2 while the living body is punctured by the distal side needle tip of the double-ended needle 71. However, when the cover member 6 is at the second position, the piercing of the distal side needle tip of the double-ended needle 71 through the sealing member 11 is not completed, and the inner side upper end face of the supporting member 72 and the distal surface of the reduced diameter portion 42b of the distal side member 4b of the outer tube 4 are in a state spaced from each other. Then, at the third position after the outer tube 4 rotates with respect to the cover member 6 and the inner tube 3, the piercing of the proximal side needle tip of the double-ended needle 71 through the sealing member 11 is completed. Thus, the inner side upper end face of the supporting member 72 and the distal surface of the reduced diameter portion 42b of the distal side member 4b of the outer tube 4 are in a state in which they contact with each other.

The cover member 6 has a bottomed tubular shape (tubular shape). The cover member 6 has a cover main body 60 depicted in FIGS. 15 and 16, and a rotor 65 depicted in FIG. 17 which is mounted on the cover main body 60 for relative rotation around the center axis of the cover main body 60 and rotates in an interlocking relationship with a pressing operation.

Figure 15:
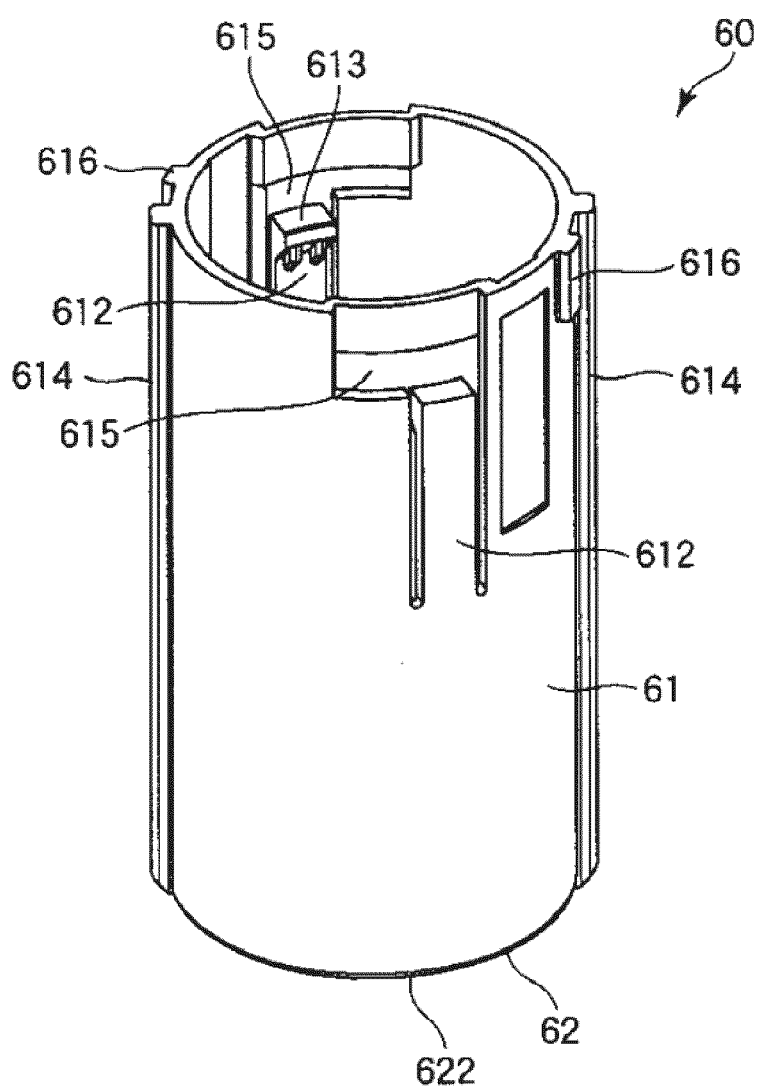
FIG. 15 is a perspective view of a cover main body of a cover member of the liquid administration tool depicted in FIG. 1.
Figure 16:
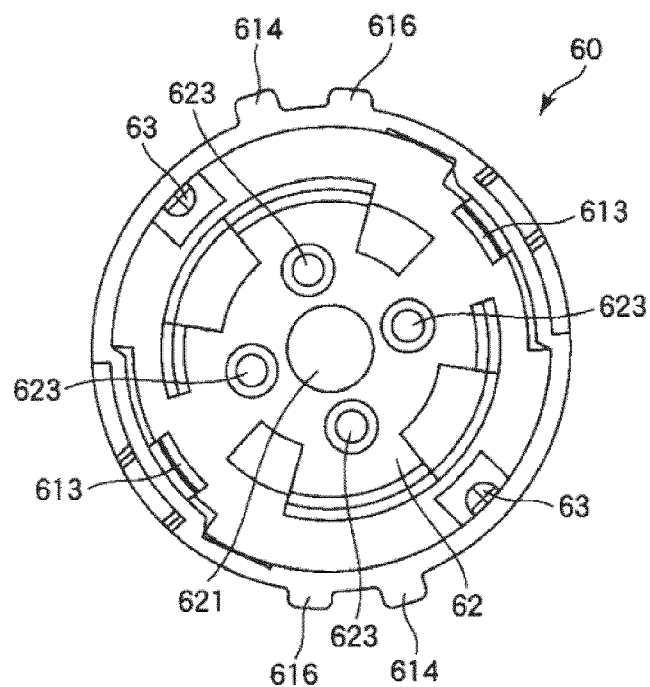
FIG. 16 is a top plan view of the cover main body of the cover member of the liquid administration tool depicted in FIG. 1.
Figure 17:
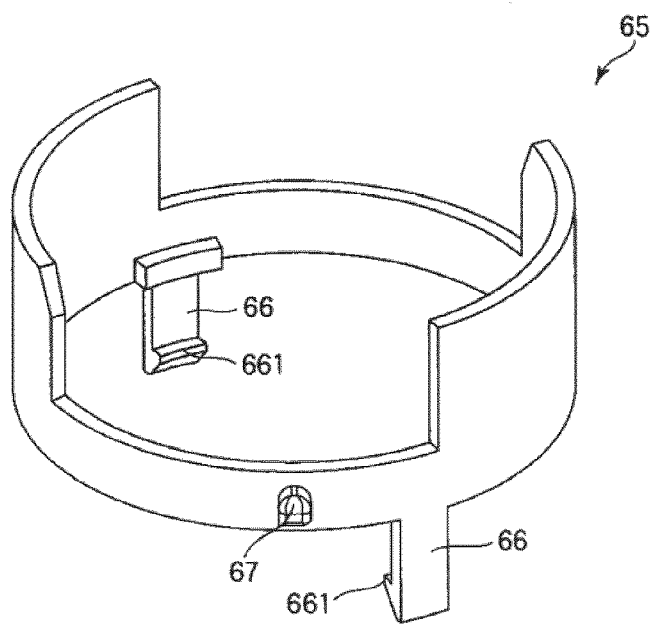
FIG. 17 is a perspective view of a rotor of the cover member of the liquid administration tool depicted in FIG. 1.

As depicted in FIGS. 15 and 16, the cover main body 60 is configured from a distal wall portion 62 in the form of a plate disposed at a distal portion thereof, and a side wall 61 provided uprightly in a direction toward the distal end from the distal wall portion 62. In other words, the cover main body 60 is configured from a member which demonstrates a bottomed tubular shape (tubular shape). The cover main body 60 further has a distal surface 622 at the distal end thereof.

An opening portion 621 is formed at a central portion of the distal wall portion 62 such that it extends through the central portion. When the cover member 6 is positioned at a position from the second to the fourth position, the distal side needle tip of the double-ended needle 71 projects (is exposed) from the opening portion 621 (refer to FIGS. 19 to 24).

Four hole portions 623 are formed at equal angular distances along a circumferential direction of the distal wall portion 62 on an outer circumference side of the opening portion 621 of the distal wall portion 62 such that they extend through the distal wall portion 62 (refer to FIG. 16). The hole portions 623 are disposed at positions corresponding to the projections 722 of the supporting member 72 of the puncture needle 7 as viewed in plan of the cover member 6 such that the projections 722 can be inserted into the hole portions 623. In a state in which the distal side needle tip of the double-ended needle 71 punctures a living body, the projections 722 are inserted in the hole portions 623. Consequently, when liquid is administrated, the puncture needle 7 can be prevented from rotationally moving in a circumferential direction.

As depicted in FIG. 15, the side wall 61 has a cylindrical shape. A pair of ribs 614 are formed on an outer circumferential face of a proximal portion of the side wall 61 such that they project to the outer side and are disposed in an opposing relationship to each other. The ribs 614 extend in the axial direction of the cover member 6. Further, a pair of ribs 616 are formed on the outer circumferential face of a proximal portion of the side wall 61 such that they project to the outer side and are disposed in an opposing relationship to each other. The ribs 616 extend in the axial direction of the cover member 6.

A pair of arm portions 612 having elasticity are formed on a portion of the side wall 61 such that they are disposed in an opposing relationship to each other and project in a direction toward the proximal end. A projection 613 is formed at a proximal portion of each of the arm portions 612 and projects toward the inner side. The projections 613 are disposed on the distal side with respect to the proximal end of the side wall 61.

A pair of projections 63 are formed on an inner circumferential face of a proximal portion of the side wall 61 such that they project to the inner side and are disposed in an opposing relationship to each other (refer to FIG. 16). The projections 63 are inserted into the cam grooves 42 of the outer tube 4, or in other words, are engaged with the cam grooves 42. The relationship between the projections 63 and the cam grooves 42 of the outer tube 4 in a sequence of operations is hereinafter described.

In the unused state (initial state), the projections 613 of the cover member 6 are individually inserted on the grooves 43b of the outer tube 4. Then, when the cover member 6 moves in an axial direction of the outer tube 4 and the outer tube 4 rotates by a predetermined angle with respect to the cover member 6 through the engagement between the cam grooves 42 of the outer tube 4 and the projections 63 of the cover member 6, the projections 613 of the cover member 6 are moved to a position on the proximal side of the elongated holes 44b in the individual spaces 45b of the outer tube 4.

Further, at a proximal portion of the side wall 61, namely, on the proximal side of each projection 613, a pair of elongated holes 615 are formed so as to be disposed in an opposing relationship to each other. The elongated holes 615 extend in a circumferential direction.

The rotor 65 has a circular ring shape (tubular shape) and is provided at a proximal portion of the cover main body 60.

A pair of arm portions 66 having elasticity are formed at a distal portion of the rotor 65 such that they are disposed in an opposing relationship to each other and project in a direction toward the distal end. A pawl 661 is formed at a distal portion of each of the arm portions 66 and projects toward the inner side. The pawls 661 are inserted in the elongated holes 615 from the outer side of the proximal side of the cover main body 60 such that the pawls 661 and the elongated holes 615 are engaged with each other to interlock the rotor 65 and the cover main body 60 with each other. The pawls 661 can move in a circumferential direction of the cover main body 60 along the elongated holes 615. Consequently, the rotor 65 can rotate relative to the cover main body 60 around the center axis of the cover main body 60. Since the rotor 65 and the cover member 6 are not integrated with each other, when the rotor 65 rotates, the contact face of the distal end of the cover member 6 can be prevented from rotating. Further, by the engagement of the pawls 661 and the elongated holes 615, the rotor 65 is prevented from moving with respect to the cover main body 60 in the direction of the center axis of the cover main body 60.

Further, a pair of projections 67 are formed on an outer circumferential face of the rotor 65 such that they project to the outer side and are disposed in an opposing relationship to each other.

As depicted in FIG. 1, the coil spring (compression coil spring) 13 is accommodated in a compressed state in the inside of the cover member 6. The coil spring 13 attaches at a distal portion thereof to the distal wall portion 62 in the inside of the cover member 6 and at a proximal portion thereof to a distal portion of the body portion 41 of the outer tube 4. The compressed state of the coil spring 13 in the unused state is such that the coil spring 13 is compressed by a load applied to the distal end of the outer tube 4. Note that the coil spring 13 need not be in a compressed state if it attaches at a distal portion thereof to the distal wall portion 62 in the inside of the cover member 6 and attaches at a proximal portion thereof to a distal portion of the body portion 41 of the outer tube 4. By the coil spring 13, for example, the cover member 6 can be biased in a direction from the second position to the first position (biased in a direction toward the distal end). By the biasing force of such a coil spring 13 as described above, the distal surface 622 of the cover member 6 can be kept projecting to the distal side from the distal side needle tip of the double-ended needle 71 until the liquid administration tool 10 is used. Therefore, puncture in error by the distal side needle tip can be prevented with certainty.

Note that the constituent material of the coil spring 13 is not limited particularly, and metal materials such as stainless steel or copper can be used.

The gasket 8 is accommodated for sliding movement along an axial direction of the inner tube 3 in the inner tube 3 (tubular body 2). It is to be noted that liquid is filled in advance in a space defined by the gasket 8 and the inner tube 3. When the gasket 8 moves in a direction toward the distal end, the liquid in the inner tube 3 can be extruded from the double-ended needle 71 which is in a state communicated with the inner tube 3.

The gasket 8 has a cylindrical outer shape and has three projections 81 formed on an outer circumferential portion thereof. Adjacent ones of the projections 81 are spaced from each other along an axial direction of the gasket 8. Further, the projections 81 have a shape of a ring along a circumferential direction of the gasket 8 and have, in a natural state thereof in which no external force is applied, an outer diameter a little greater than the inner diameter of the inner tube 3. Consequently, the projections 81 can individually slidably move while closely contacting with an inner circumferential portion of the side wall 33 of the inner tube 3. Therefore, the liquid tightness can be maintained with certainty and improvement of the sliding performance can be anticipated.

As depicted in FIGS. 1 to 3, the operation member 5 has a head portion 53, a grasping portion (outermost tube) 52, and a pusher 51 interlocked to the proximal side of the gasket 8 and configured to push the gasket 8 in a direction toward the distal end. The head portion 53, the pusher 51, and the grasping portion 52 are interlocked with each other. The operation member 5 is a member which performs, when the pusher 51 moves in the direction toward the distal end to move the gasket 8 in the direction toward the distal end, a pushing operation (discharging operation) for discharging the liquid in the inner tube 3 from the double-ended needle 71.

Figure 4:
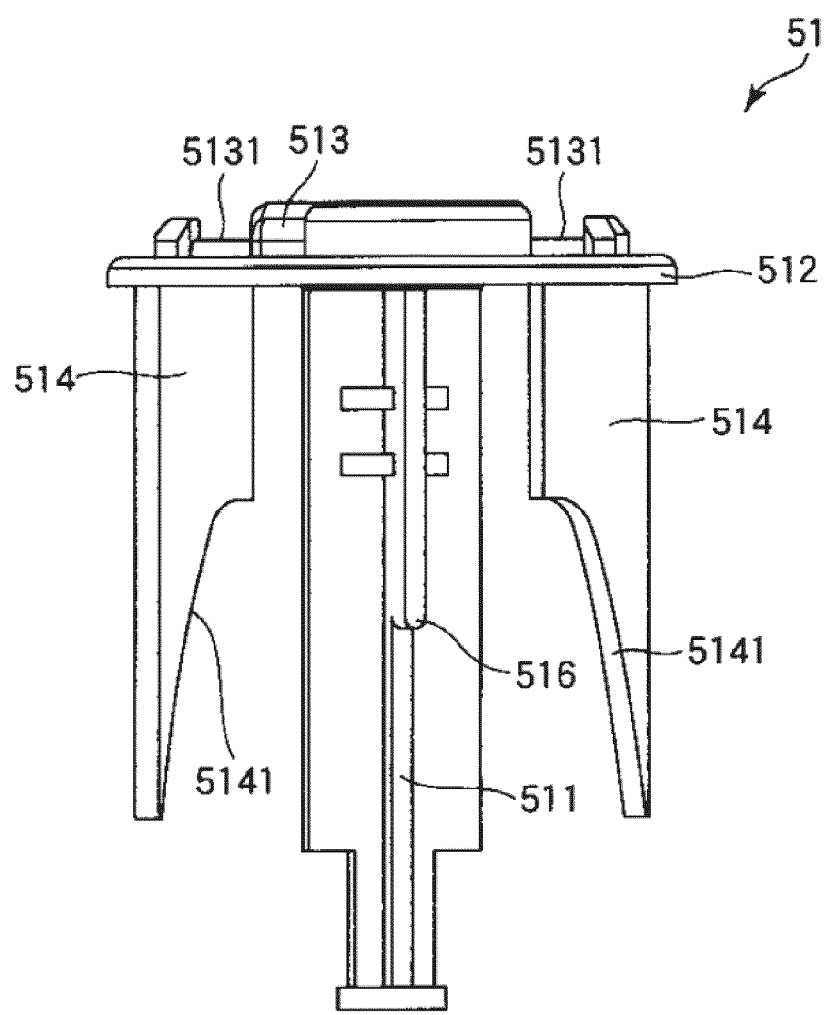
FIG. 4 is a lateral view of a pusher of an operation member of the liquid administration tool depicted in FIG. 1.
Figure 5:
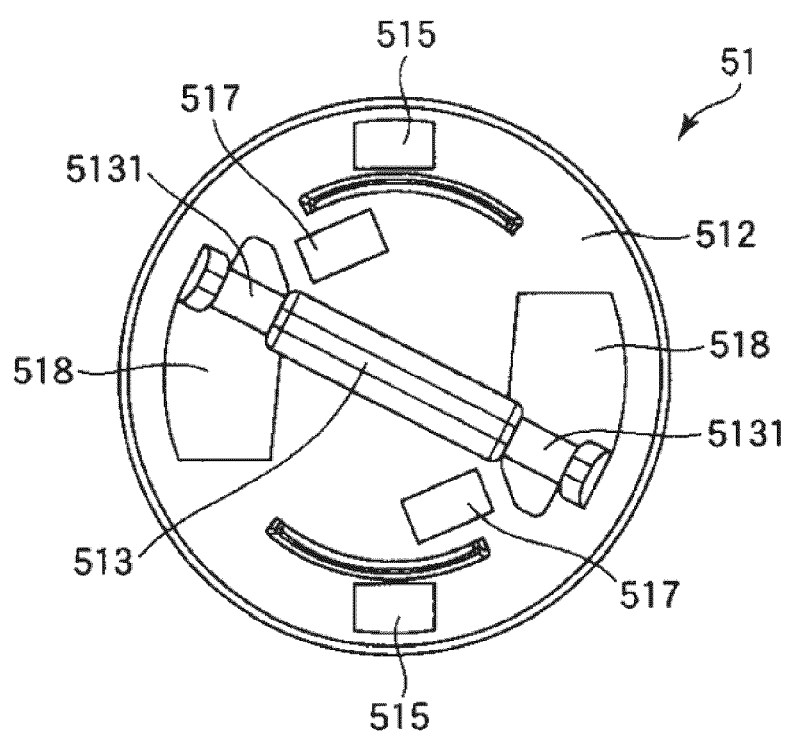
FIG. 5 is a top plan view of the pusher of the operation member of the liquid administration tool depicted in FIG. 1.

As depicted in FIGS. 1, 4, and 5, the pusher 51 has a main body portion 511 in the form of a bar having, for example, a cross-shaped or circular transverse section, and the gasket 8 is fixed to the distal end of the main body portion 511. A flange 512 in the form of a disk is formed at the proximal end of the main body portion 511.

The method of fixing the gasket 8 to the main body portion 511 is not limited particularly. For example, a method by adhesion or fusion, a method of forming a recessed portion on the gasket 8, setting the shape of a distal portion of the main body portion 511 to a shape corresponding to the recessed portion of the gasket 8, and inserting the distal portion of the main body portion 511 into the recessed portion of the gasket 8, a method of forming a male thread at a distal portion of the main body portion 511, forming a female thread for engaging with the male thread on the gasket 8, and causing the threads to engage with each other and so forth are available. Note that, although the operation member 5 in the present embodiment is interlocked to the proximal side of the gasket 8, it may not be interlocked.

The flange 512 of the pusher 51 has formed thereon a pair of hole portions 515 disposed in an opposing relationship to each other across the center thereof, another pair of hole portions 517 disposed in an opposing relationship to each other across the center, and a further pair of hole portions 518 disposed in an opposing relationship to each other across the center.

A rib 513 is formed at a central portion of the proximal side of the flange 512 such that it extends in a radial direction of the flange 512 and extends between the hole portions 518. A groove 5131 is formed at the opposite end portions of the rib 513, namely, at locations corresponding to the hole portions 518.

Further, a pair of projecting pieces 514 are formed on a lower face of the flange 512 such that they project in a direction toward the distal end and are disposed in an opposing relationship to each other. The projecting pieces 514 are disposed symmetrically with respect to a point as viewed in plan of the pusher 51 (as viewed from the upper side in FIG. 4). Since the projecting pieces 514 are similar in configuration, the following description is given of one of the projecting pieces 514 as a representative. Note that the projecting pieces 514 may be disposed on the grasping portion (outermost tube) 52.

The projecting piece 514 has a length which varies along a circumferential direction of the flange 512 such that an inclined face (attaching face) 5141 inclined along the circumferential direction of the flange 512 is formed at the distal end of the projecting piece 514. Further, the length of the projecting piece 514 decreases gradually toward a clockwise direction as viewed in plan of the pusher 51. Upon a pressing operation, the projection 67 of the rotor 65 is attached to the inclined face 5141 of the projecting pieces 514 to rotate the rotor 65 clockwise as viewed in plan of the pusher 51. Consequently, drug solution can be administrated with certainty with the resistance to pushing reduced. Further, if a step is provided on the inclined face 5141 of the projecting piece 514 of the operation member 5, then sound is generated upon contact of the rotor 65 with the projection 67. This makes it possible to allow the user to recognize that drug solution is being administrated. Further, as hereinafter described, if the pushing operation is stopped and the operation member 5 is moved in a direction toward the proximal end, then the projection 67 is attached to a bottom portion 5242 of a staircase 524. Consequently, the cover member 6 can be prevented from being locked by a locking unit 50.

Further, the main body portion 511 of the pusher 51 has a plate-shaped portion having a longitudinal shape and has, as first engaging portions engageable with a pair of projections (second engaging portions) 49a, a pair of step portions 516 of a width varied from that of the plate-formed portion. In particular, a pair of step portions (first engaging portions) 516 are formed on the distal side of the main body portion 511 of the pusher 51 such that they are disposed in an opposing relationship to each other. The step portions 516 and the projections 49a configure engaging portions which assume, when they are engaged with each other, an engaged state in which the pressing operation is blocked and assume, when the engaging state is canceled, a disengaged state in which the pressing operation is permitted.

Note that the number of step portions (first engaging portions) 516 is not limited to two but may be one or three or more.

Alternatively, the step portions (first engaging portions) may be provided on the inner side structure body 1, and the projections (second engaging portions) may be provided on the operation member 5.

In the unused state (initial state), the step portions 516 of the pusher 51 are positioned such that they engage or can engage with the projections 49a of the outer tube 4, and consequently, movement of the pusher 51 in the direction toward the distal end with respect to the tubular body 2 is blocked. Then, when the cover member 6 moves in an axial direction of the outer tube 4 and the cam grooves 42 of the outer tube 4 and the projections 63 of the cover member 6 move the outer tube 4 to a position at which the outer tube 4 can rotate by a predetermined angle with respect to the cover member 6, the step portions 516 of the pusher 51 move to a position displaced from the projections 49a of the outer tube 4. Along with this, the engagement between the step portions 516 and the projections 49a is cancelled, whereby movement of the pusher 51 in the direction toward the distal end with respect to the tubular body 2 is permitted.

Figure 6:
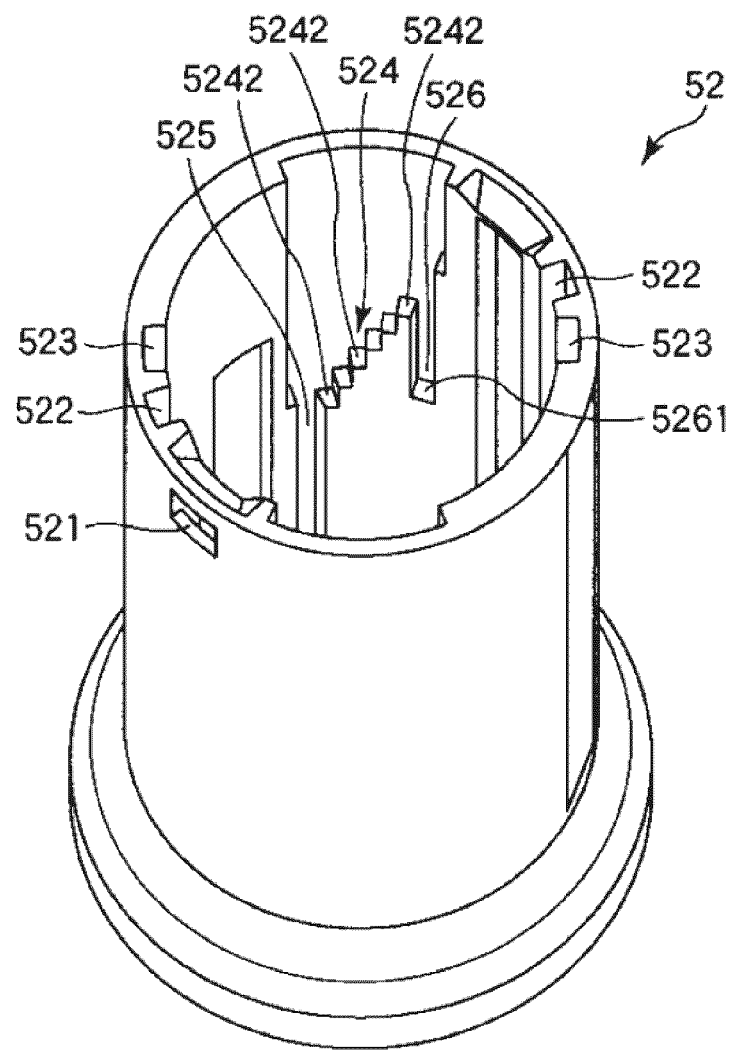
FIG. 6 is a perspective view of a grasping portion of the operation member of the liquid administration tool depicted in FIG. 1.
Figure 7:
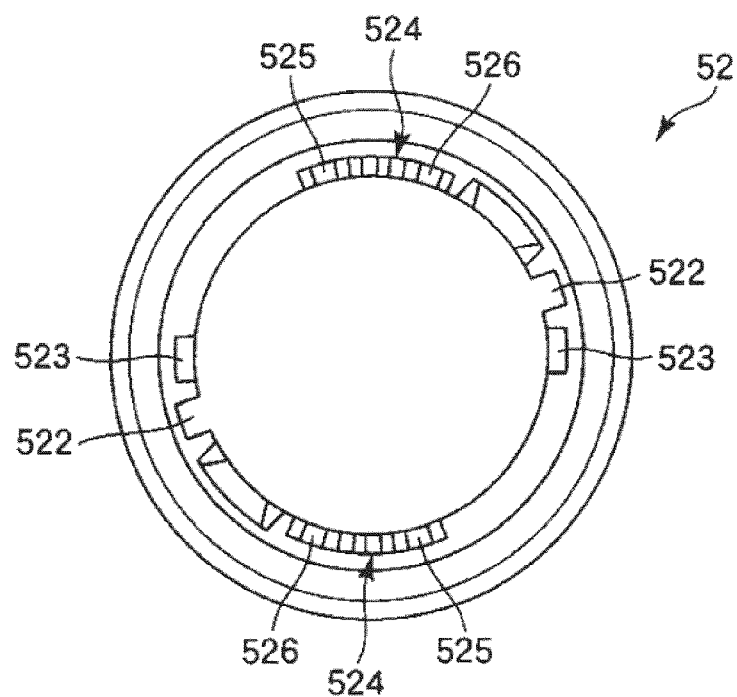
FIG. 7 is a top plan view of the grasping portion of the operation member of the liquid administration tool depicted in FIG. 1.

As depicted in FIGS. 1, 6, and 7, the grasping portion 52 is disposed on the outer periphery side of the main body portion 511 of the pusher 51, the inner side structure body 1, and the cover member 6, and the flange 512 of the pusher 51 attaches to the proximal end of the grasping portion 52. The grasping portion 52 has a cylindrical shape and is a portion which is grasped upon use.

Further, a pair of hole portions 521 are formed at a proximal portion of the grasping portion 52 and disposed in an opposing relationship to each other.

Further, a pair of grooves 522 are formed on an inner circumferential face of the grasping portion 52 and disposed in an opposing relationship to each other. The grooves 522 extend along an axial direction of the grasping portion 52. In the grooves 522, the ribs 614 of the cover member 6 are inserted. Consequently, rotation of the cover member 6 with respect to the grasping portion 52 is prevented.

Further, a pair of grooves 523 are formed on an inner circumferential face of the grasping portion 52 and disposed in an opposing relationship to each other. The grooves 523 extend along the axial direction of the grasping portion 52. In the grooves 523, the ribs 616 of the cover member 6 are inserted. Consequently, when the cover member 6 moves in the direction toward the distal end with respect to the grasping portion 52, the ribs 616 of the cover member 6 are attached to distal portions of the grooves 523 of the grasping portion 52 to prevent the cover member 6 from being separated from the grasping portion 52.

A pair of staircases (engaging portions) 524 are formed on an inner circumferential face of the grasping portion 52 such that they are disposed in an opposing relationship to each other and the pair of projections 67 of the rotor 65 are engageable therewith. Movement of the cover member 6 in the direction toward the distal end is blocked by attachment of the projections 67 to a predetermined stage of the staircases 524. The staircases 524 are disposed in a symmetrical relationship with respect to a point as viewed in plan of the grasping portion 52 (as viewed from the upper side in FIG. 6). Note that, since the staircases 524 are similar to each other, description of one of the staircases 524, namely, of the staircase 524 observable in FIG. 6, is given below as a representative.

The staircase 524 is configured such that, if it is followed in a clockwise direction in FIG. 6 which is the direction of rotation of the rotor 65 as viewed in plan of the grasping portion 52, then it exhibits a rise from the distal side toward the proximal side. In particular, the height of the staircase 524 gradually increases toward a clockwise direction as viewed in plan of the grasping portion 52. In other words, the staircase 524 can be considered as a portion whose distance in the axial direction from the proximal end of the operation member 5 gradually decreases stepwise toward the clockwise direction.

Further, the heights of the steps of the staircases 524 demonstrate a fixed increasing amount in height and are set such that, in a state in which the projections 67 of the rotor 65 engage with the stages of the staircase 524, the projections 613 of the cover member 6 are positioned on the proximal side with respect to the elongated holes 44b of the outer tube 4. Note that it is a matter of course that the increasing amount in height of the stages of the staircase 524 may not be fixed.

Figure 19:
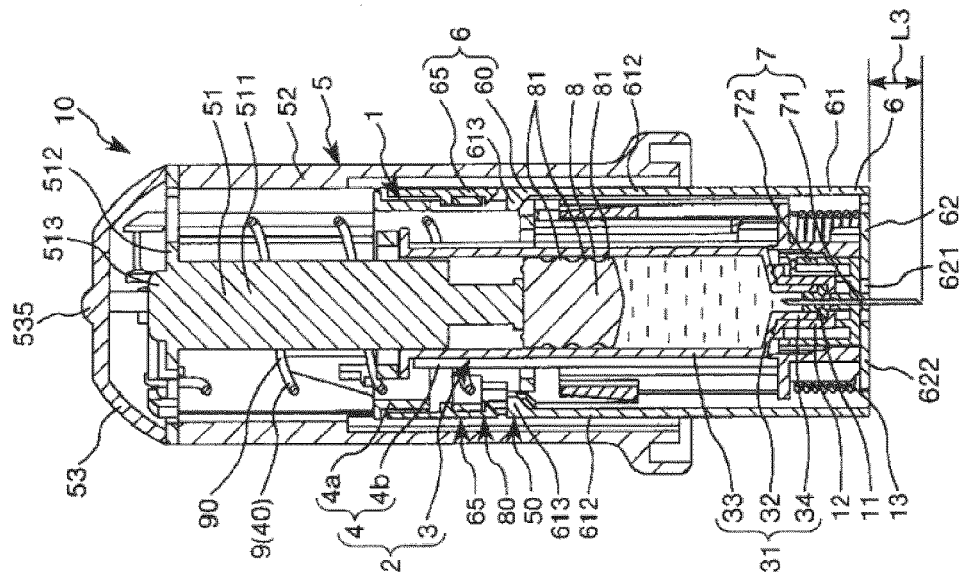
FIG. 19 is a vertical sectional view depicting operational state in order upon use of the liquid administration tool depicted in FIG. 1.
Figure 21:
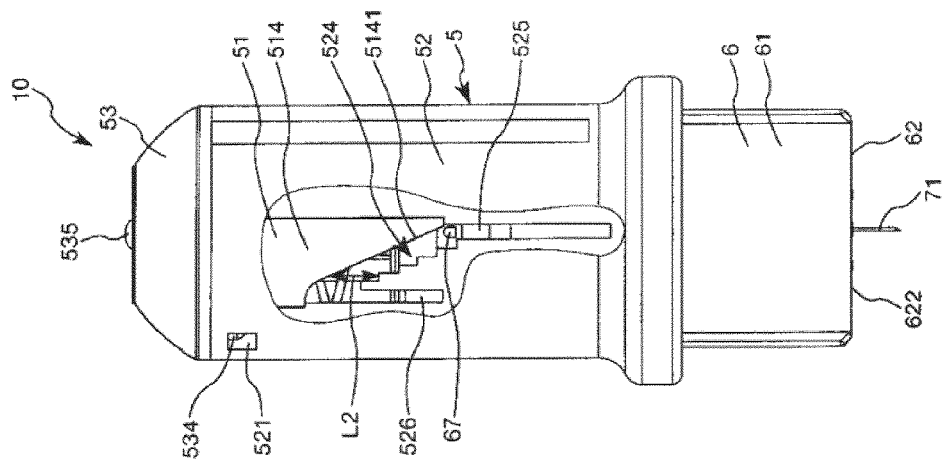
FIG. 21 is a lateral view depicting operational state in order upon use of the liquid administration tool depicted in FIG. 1.
Figure 28:
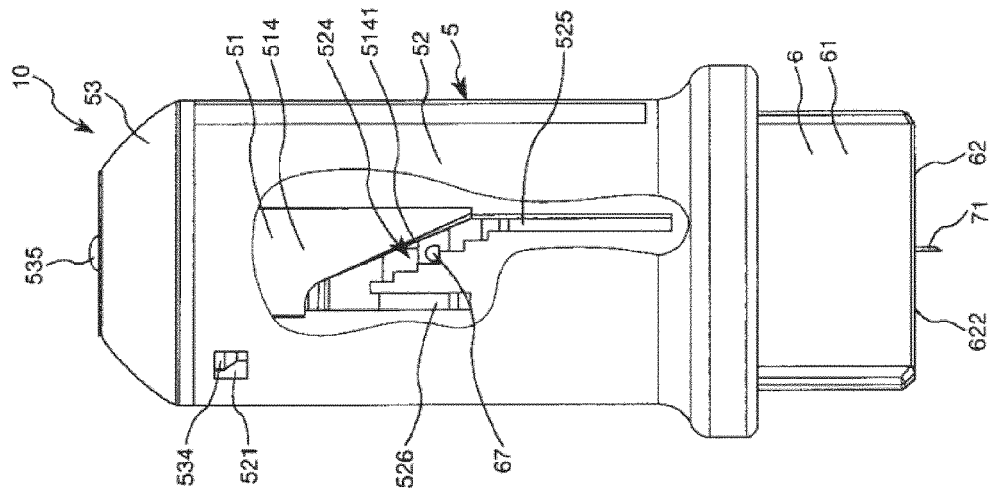
FIG. 28 is a lateral view depicting operational state in order upon use of the liquid administration tool depicted in FIG. 1.

Further, in the state in which the projections 67 of the rotor 65 engage with the staircases 524, the distal side needle tip of the double-ended needle 71 may be exposed from the distal end of the cover member 6 (refer to FIG. 29) or may not be exposed (refer to FIG. 28). In order to prevent the distal side needle tip of the double-ended needle 71 from being exposed, the height of the stages of the staircases 524 is set comparatively low, namely, the distance between the inclined faces 5141 of the projecting pieces 514 of the pusher 51 and the stages of the staircases 524 is set comparatively great. In particular, if the projection length of the double-ended needle 71 from the distal wall portion 62 of the cover member 6 upon administration of liquid, namely, the distance between the distal surface of the distal wall portion 62 of the cover member 6 and the distal end of the double-ended needle 71, is represented by L3 as depicted in FIG. 19 and the distance between the bottom portion 5242 of the staircase 524 of the grasping portion 52 and the inclined face 5141 of the projecting piece 514 of the pusher 51 is represented by L2 as depicted in FIG. 21, then the distal side needle tip of the double-ended needle 71 is not exposed if L2≥L3 is satisfied.

On the other hand, in order to cause the distal side needle tip of the double-ended needle 71 to be exposed, the height of the stages of the staircases 524 is set comparatively high, namely, the distance between the inclined faces 5141 of the projecting pieces 514 of the pusher 51 and the stages of the staircases 524 is set comparatively small. In particular, if L2<L3 is satisfied, then the distal side needle tip of the double-ended needle 71 is exposed.

Note that, where the distal side needle tip of the double-ended needle 71 is not exposed, since the distal side needle tip of the double-ended needle 71 is covered with the cover member 6, puncture in error by the distal side needle tip of the double-ended needle 71 can be prevented with certainty.

Further, a groove 525 is formed on the left side of the staircase 524 in FIG. 6, and another groove 526 is formed on the right side. Also on the opposite sides of the other staircase, grooves 525 and 526 are formed. In particular, a pair of grooves 525 and a pair of grooves 526 are formed on an inner circumferential face of the grasping portion 52 such that the grooves 525 are disposed in an opposing relationship to each other and the grooves 526 are disposed in an opposing relationship to each other. The grooves 525 and 526 extend along the axial direction of the grasping portion 52. Note that, in the unused state (initial state), the projections 67 of the rotor 65 are positioned in the grooves 525.

Figure 8:
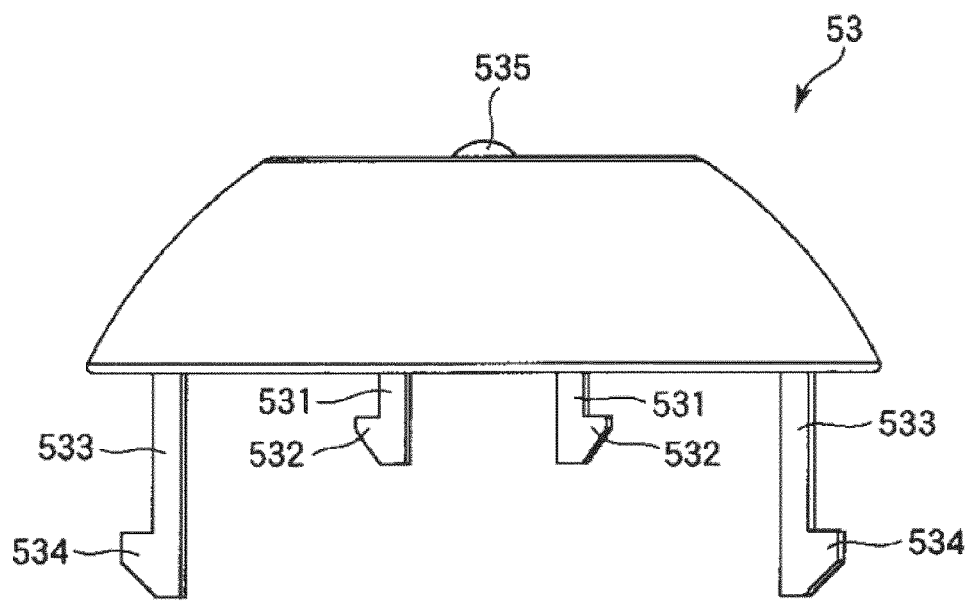
FIG. 8 is a lateral view of a head portion of the grasping portion of the liquid administration tool depicted in FIG. 1.
Figure 9:
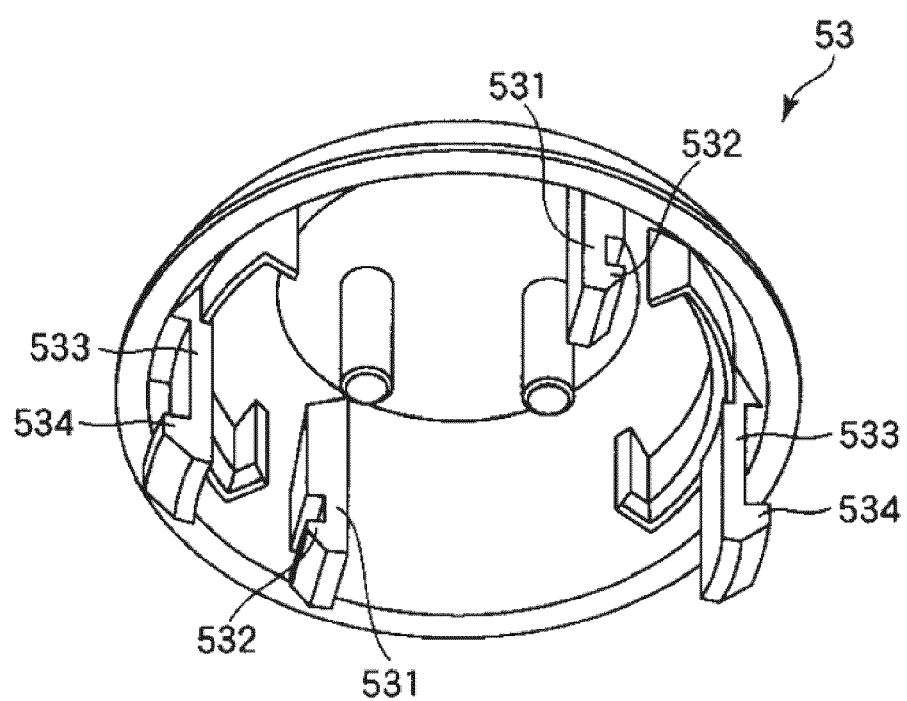
FIG. 9 is a perspective view of the head portion of the grasping portion of the liquid administration tool depicted in FIG. 1.

The head portion 53 is provided on the proximal side of the grasping portion 52 and the flange 512 of the pusher 51. As depicted in FIGS. 1, 8, and 9, the head portion 53 has a conical shape. A proximal surface, namely, an outer face, of the head portion 53 is flat at a central portion thereof, and a peripheral portion of the head portion 53 is curved such that the proximal side thereof is projected. Since the head portion 53 has the curved face, the operation member 5 can be grasped easily by one hand. Further, since the flat face is formed at a central portion of the head portion 53, when a pressing operation is performed by both hands, the pressing operation can be performed easily.

Further, a projection 535 is formed at the center of the proximal surface of the head portion 53. Consequently, even if it is tried to place the liquid administration tool 10 on a table such that the head portion 53 thereof is positioned on the lower side in the vertical direction, the liquid administration tool 10 will fall down. Consequently, the liquid administration tool 10 can be prevented from being grasped with the distal end and the proximal end reversed.

Further, a pair of arm portions 531 having elasticity are formed on an outer peripheral portion of a distal surface of the head portion 53, namely, of an inner face of the head portion 53, such that they are disposed in an opposing relationship to each other and project in a direction toward the distal end. Further, a pawl 532 is formed at a distal portion of each of the arm portions 531 such that it projects to the outer side. Further, a pair of arm portions 533 having elasticity are formed on an outer peripheral portion of the distal surface, namely, of the inner face, of the head portion 53 such that they are disposed in an opposing relationship to each other and project in a direction toward the distal end. A pawl 534 is formed at a distal portion of each of the arm portions 533 and projects to the outer side.

Thus, if the pawls 532 of the arm portions 531 of the head portion 53 are inserted into the hole portions 518 until they are engaged with each other, then the head portion 53 and the pusher 51 are interlocked with each other. Further, if the pawls 534 of the arm portions 533 of the head portion 53 are inserted into the hole portions 521 from the inner side of the grasping portion 52 until they are engaged with each other, then the head portion 53 and the grasping portion 52 are interlocked with each other.

The auxiliary unit 40 has a function of generating assisting force (pressing force) for pressing the gasket 8 through the pusher 51 of the operation member 5. As depicted in FIG. 1, in the present embodiment, the auxiliary unit 40 has a coil spring 9 serving as a biasing member. The coil spring 9 is a tension spring which is used in an extended state. The coil spring 9 has a coil spring main body 90, a hook (not depicted) which is a first mounting portion provided at a distal portion of the coil spring main body 90 and mounted on the inner side structure body 1, and another hook (not depicted) which is a second mounting portion provided at a proximal portion of the coil spring main body 90 and mounted on the operation member 5.

Although the shape of the hooks is not limited particularly, in the present embodiment, the hooks have, for example, a U shape. Note that other shapes such as, for example, a V shape or a channel shape may be applied.

Further, the pusher 51 is disposed in the inside of the coil spring 9 as viewed in the axial direction of the coil spring 9. The coil spring 9 is wound on an outer periphery of the pusher 51. In particular, the pusher 51 and the tubular body 2 are disposed concentrically on the outer periphery side of the pusher 51. The coil spring 9 is hooked, in an extended state, at a hook thereof on the supporting portion 43 of the outer tube 4 and at the other hook thereof in the groove 5131 of the rib 513 of the pusher 51.

Consequently, the coil spring 9 biases the inner side structure body 1 and the operation member 5 in directions in which they approach each other. In particular, the coil spring 9 exerts assisting force for pressing the gasket 8 in the direction toward the distal end through the pusher 51 of the operation member 5. Consequently, upon a pressing operation, the operation member 5 can be moved easily in the direction toward the distal end.

Here, if the biasing force (pressing force) of the coil spring 9 is represented by F1, the biasing force of the coil spring 13 is represented by F2, and the drug solution discharge resistance of the gasket 8 with respect to the inner tube 3 (tubular body 2) during sliding movement is represented by F0, then F0 and F1 are set so as to satisfy the following expression (1):

$$F1 \leq F0 \quad (1)$$

Consequently, when liquid is administrated, the pusher 51 can be prevented from automatically moving in the direction toward the distal end to administrate liquid while the user does not apply force for slidably moving the gasket 8. In other words, the user can perform administration of liquid as intended by the user and can administrate liquid in accordance with a pace of the user. Further, if the user wants to interrupt administration of liquid, then the administration of liquid can be interrupted instantly.

Further, the biasing force F1 preferably ranges from 1 N to 40 N and more preferably is 1 N to 10 N. Where the biasing force F1 is lower than the lower limit value of 1 N, depending upon some other condition, there is the possibility that the assisting force may be insufficient. On the other hand, if the biasing force F1 is higher than the upper limit value of 40 N given above, then depending upon some other condition, the biasing force F2 becomes small, and there is the possibility that distal side needle tip of the double-ended needle 71 is exposed from the distal end of the cover 6.

Meanwhile, the biasing force F2 preferably is 1 N to 5 N, and more preferably is 1 N to 3 N. If the biasing force F2 is lower than the lower limit value of 1 N, then depending upon some other condition, there is the possibility that the distal side needle tip of the double-ended needle 71 is exposed from the distal end of the cover member 6. On the other hand, if the biasing force F2 is higher than the upper limit value of 5 N, then depending upon some other condition, it is difficult to move the cover member 6 in the direction toward the proximal end against the biasing force of the coil spring 13.

It is to be noted that the constituent material of the coil spring 9 is not limited particularly, and, for example, a constituent material similar to that of the coil spring 13 can be used.

The locking unit 50 has a function of restricting, when the cover member 6 is moved from the position (B) to the position (A) by the biasing force of the coil spring 13 until the movement amount of the cover member 6 reaches a lock permitting movement amount, further movement of the cover member 6 to the position (B).

As depicted in FIGS. 1, 12, and 15, in the present embodiment, the locking unit 50 has the aforementioned projection 613 of the cover member 6 and the elongated holes 44*b* of the outer tube 4. If the movement amount of the cover member 6 reaches the lock permitting movement amount and the projections 613 are engaged with the proximal portion of the elongated holes 44*b*, then the movement of the cover member 6 in the direction toward the proximal end with respect to the outer tube 4 is blocked.

The movement amount restriction unit 80 has a function of restricting the movement amount of the cover member 6 so that the movement amount when the cover member 6 is positioned at the position (B) and the cover member 6 is moved in the direction toward the distal end by the biasing force of the coil spring 13 cannot reach the lock permitting movement amount until the pressing operation is completed.

As depicted in FIGS. 1, 4, 6, and 17, in the present embodiment, the movement amount restriction unit 80 includes the aforementioned pair of projections 67 of the rotor 65, the pair of staircases 524 of the grasping portion 52 of the operation member 5, and the pair of projecting pieces 514 of the pusher 51 of the operation member 5. The dimensions of different portions of the movement amount restriction unit 80 are set such that, where the distance between the proximal ends of the elongated holes 44*b* of the outer tube 4 and the projections 613 of the cover member 6 is represented by L1 (for the projections 613, refer to FIG. 15) as depicted in FIG. 12 and the distance between the bottom portions 5242 of the staircases 524 of the grasping portion 52 and the inclined faces 5141 of the projecting pieces 514 of the pusher 51 is represented by L2 as depicted in FIG. 21, the relationship of L1>L2 is satisfied. Consequently, if a pressing operation is interrupted in administration of liquid and the distal wall portion 62 of the cover member 6 is separated from the living body and the double-ended needle 71 is pulled out from the living body, then the movement amount restriction unit 80 operates such that the projections 67 of the cover member 6 attach, in a state in which the projections 613 of the cover member 6 are positioned on the proximal side with respect to the elongated holes 44*b* of the outer tube 4, to a predetermined stage of the staircases 524 of the operation member 5 to block movement of the cover member 6 in the direction toward the distal end. By this, the projections 613 of the cover member 6 are prevented from engaging with the proximal portion of the elongated holes 44*b*.

Now, a method of use of the liquid administration tool 10 and operation states of the liquid administration tool 10 when used are described with reference to FIGS. 1 to 3 and 19 to 29.

[1] As depicted in FIGS. 1 to 3, a liquid administration tool 10 in an unused state (initial state) is prepared. In the liquid administration tool 10 in the unused state, the cover member 6 is positioned at the first position and covers the distal side needle tip of the double-ended needle 71. Note that, in the unused state, the state in which the distal side needle tip of the double-ended needle 71 is covered with the cover member 6 is maintained by the biasing force of the coil spring 13. Consequently, puncture in error by the distal side needle tip of the double-ended needle 71 can be prevented with certainty.

Further, the puncture needle 7 does not puncture the sealing member 11 with the distal side needle tip of the double-ended needle 71 thereof spaced from the sealing member 11 of the inner tube 3 of the tubular body 2.

Consequently, the sterile condition of the liquid can be maintained until administration of the drug solution is started.

Further, the projections 63 of the cover member 6 are positioned at the position depicted in FIG. 2 with respect to the outer tube 4.

Further, the projections 613 of the cover member 6 are positioned on the proximal side of the grooves 43b at the distal portion of the outer tube 4.

Further, the step portions 516 of the pusher 51 are positioned such that they attach to the inclined faces 491a of the projections 49 of the outer tube 4 or they can attach to the inclined faces 491a (they may be spaced from the inclined faces before use of the liquid administration tool 10). Namely, the step portions 516 are positioned such that they engage or can engage with the projections 49a. Consequently, movement of the operation member 5 in the direction toward the distal end with respect to the inner side structure body 1 (tubular body 2) is blocked.

Further, the projections 63 are inserted in the linear grooves 421 so that the outer tube 4 is prevented from rotating with respect to the cover member 6. Consequently, the outer tube 4 is prevented from rotating with respect to the operation member 5.

Further, the projections 67 of the rotor 65 are positioned in the grooves 525 of the operation member 5.

[2] Then, the operation member 5 of the liquid administration tool 10 in the unused state would be grasped and operated to attach the distal wall portion 62 of the cover member 6 to a living body and then pressed in the direction toward the distal end (to press the cover main body 60 against the surface of the living body). Consequently, the cover member 6 moves in the direction toward the proximal end with respect to the operation member 5 and the inner side structure body 1 against the biasing force of the coil spring 13, namely, from the first position to the second position. Further, during the process of the movement, the distal wall portion 62 of the cover member 6 is moved to the proximal portion side of the supporting member 72 of the puncture needle 7.

At this time, the distal side needle tip of the double-ended needle 71 projects from the opening portion 621 of the distal wall portion 62 of the cover member 6 to perform puncture of the living body with the distal side needle tip. Further, the distal wall portion 62 presses the supporting member 72 of the puncture needle 7 in the direction toward the proximal end. Consequently, the proximal side needle tip of the puncture needle 7 can puncture the sealing member 11 of the inner tube 3, and consequently, the double-ended needle 71 puncturing the living body and the inner tube 3 are communicated with each other.

At this time, the projections 63 of the cover member 6 move in the direction toward the proximal end relative to the outer tube 4 along the linear grooves 421. Then, when the cover member 6 is positioned at the second position, the projections 63 of the cover member 6 are positioned at the proximal portion of the linear grooves 421.

Further, at this time, the projections 613 of the cover member 6 are in a state positioned in the spaces 45b (refer to FIG. 12) on the proximal side of the grooves 43b through the movement in the direction toward the proximal end along the grooves 43b of the outer tube 4.

Further, the projections 722 of the puncture needle 7 are inserted in the hole portions 623 of the cover member 6 to prevent the puncture needle 7 from rotationally moving in a circumferential direction.

Further, at this time, the projections 721 of the puncture needle 7 are positioned in the horizontal grooves 422b and the projections 723 are positioned in the horizontal grooves 423b.

Further, the projections 63 are positioned at the proximal portion of the linear grooves 421. Consequently, the outer tube 4 is permitted to rotate with respect to the cover member 6 and therefore can rotate with respect to the operation member 5.

Further, the projections 67 are positioned at the proximal portion of the grooves 525 through the movement in a direction toward the proximal end.

Figure 20:
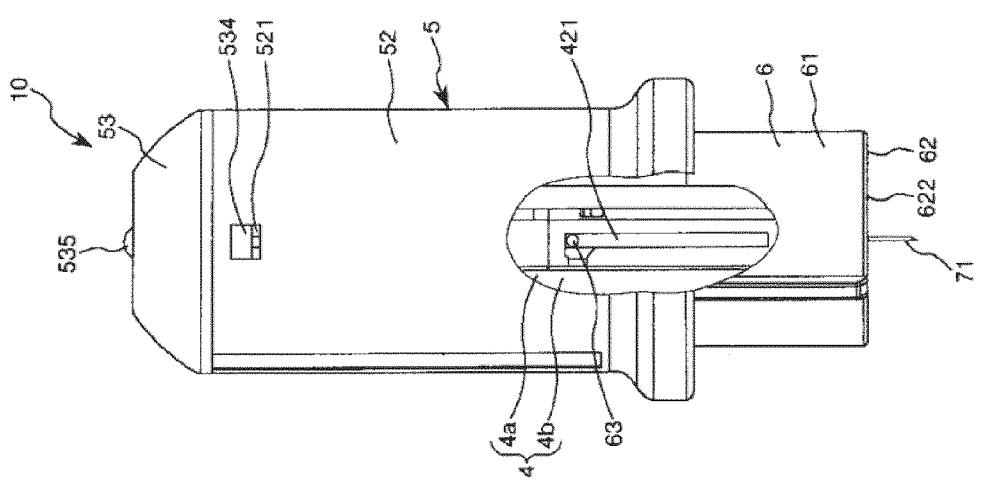
FIG. 20 is a lateral view depicting operational state in order upon use of the liquid administration tool depicted in FIG. 1.

[3] Then, the operation member 5 continues to be pressed in the direction toward the proximal end until the cover member 6 reaches the third position (refer to FIGS. 19 to 21). This is a state after the outer tube 4 is rotated fully by a predetermined angle with respect to the cover member 6 and the inner tube 3 by the cam grooves 42 of the outer tube 4 and the projections 63 of the cover member 6. Note that FIGS. 19 to 21 depict a state in which administration of liquid is started.

At this time, the step portions 516 of the pusher 51 move along the inclined faces 491a of the projections 49a, whereupon the outer tube 4 acquires driving force in the rotation direction. Further, the outer tube 4 acquires driving force in the rotation direction by the biasing force of the coil spring 9 in the rotation direction. Consequently, the outer tube 4 can be rotated easily.

Consequently, the step portions 516 of the pusher 51 move to positions displaced from the projections 49a of the outer tube 4 into a state in which the engagement between the step portions 516 and the projections 49a is cancelled. Consequently, movement of the operation member 5 in the direction toward the distal end with respect to the tubular body 2 is permitted. Thereafter, the state in which the engagement between the step portions 516 and the projections 49a is cancelled is maintained, and therefore, description of later operation of this is omitted.

Note that the puncture action of the living body by the double-ended needle 71, the rotating action of the outer tube 4, and a pressing operation of the operation member 5 hereinafter described can be performed smoothly as a single continuous action.

Further, as described hereinabove, the projections 721 of the puncture needle 7 are positioned in the horizontal grooves 422b, and the horizontal grooves 422b can move relative to the outer tube 4. Further, the projections 723 are positioned in the horizontal grooves 423b and can move in the horizontal grooves 423b relatively to the outer tube 4. Consequently, the outer tube 4 can rotate without rotating the puncture needle 7.

Further, the projections 63 of the cover member 6 move in an obliquely upward direction relative to the outer tube 4 along the inclined grooves 422. Then, when the cover member 6 is positioned at the third position, the projections 63 of the cover member 6 are positioned at an end portion of the inclined grooves 422 on the right side in FIG. 20.

Further, the projections 613 of the cover member 6 at this time are in a state in which they are positioned on the proximal side of the elongated holes 44b in the spaces 45b through rotation.

Further, the projections 67 are positioned at the proximal portion of the grooves 525.

Figure 22:
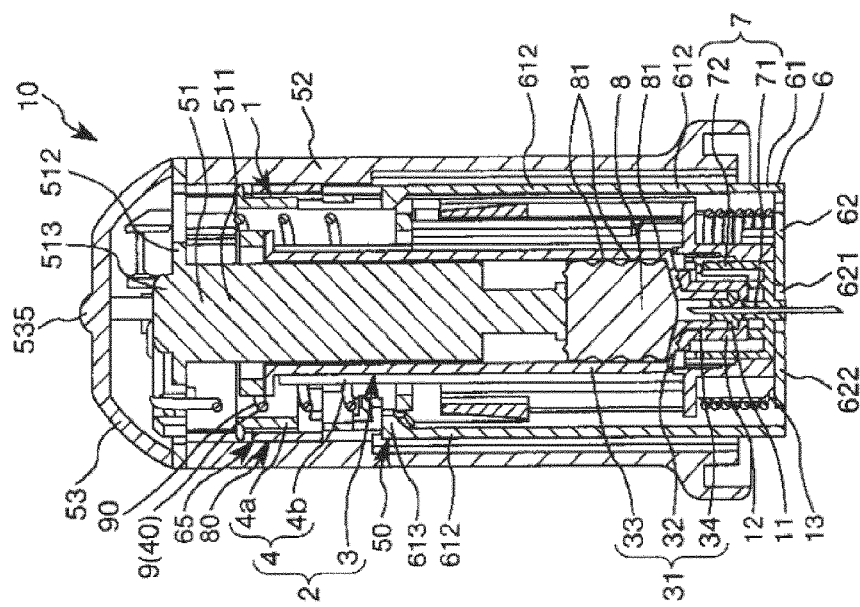
FIG. 22 is a vertical sectional view depicting operational state in order upon use of the liquid administration tool depicted in FIG. 1.

[4] In the state in which the cover member 6 is positioned at the third position, the operation member 5 is moved in the direction toward the distal end, by the pressing force of the user and the biasing force of the coil spring 9, namely, the assisting force (pressing force). Consequently, the gasket 8 is permitted to move in the direction toward the distal end. In other words, the aforementioned pressing operation is performed, and administration of liquid can be performed. Then, the gasket 8 attaches to the bottom portion 32 of the inner tube 3 as depicted in FIGS. 22 to 24, whereupon the administration of liquid is completed, namely, the pressing operation is completed, and the cover member 6 is positioned at the fourth position.

Figure 23:
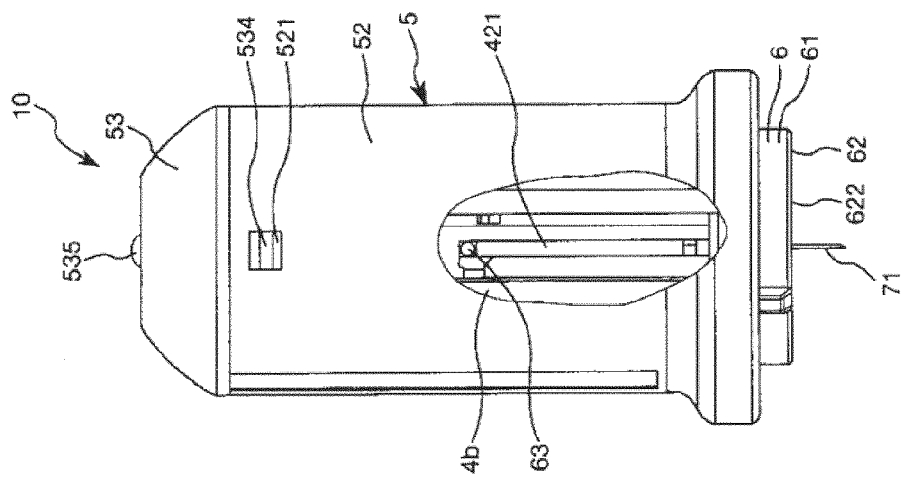
FIG. 23 is a lateral view depicting operational state in order upon use of the liquid administration tool depicted in FIG. 1.
Figure 24:
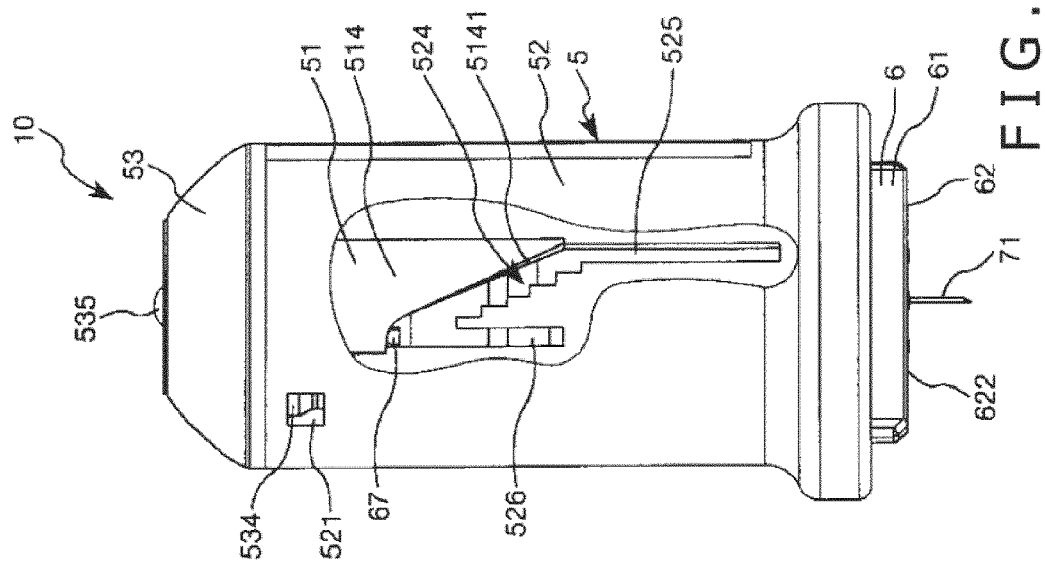
FIG. 24 is a lateral view depicting operational state in order upon use of the liquid administration tool depicted in FIG. 1.

At this time, the projections 63 of the cover member 6 remain positioned at the end portion of the inclined grooves 422 on the right side in FIG. 23.

Also the projections 613 of the cover member 6 remain positioned at the position in the spaces 45*b* on the proximal side of the elongated holes 44*b*.

Further, the pawls 47*a* of the arm portions 46*a* of the outer tube 4 are inserted into the hole portions 517 of the pusher 51 and engaged with the hole portions 517. Along with this, the arm portions 46*a* are curved once and then return, at the moment at which the pawls 47*a* project in the direction toward the distal end from the hole portions 517, to their original shape by the elasticity, whereupon sound (audible sound) and vibration (click feeling) are generated from the arm portions 46*a*. Consequently, the user can recognize that the administration of liquid (pressing operation) is completed.

Further, after the use, the outer tube 4 and the operation member 5 are fixed to each other by engagement between the pawls 47*a* and the hole portions 517. Consequently, movement of the operation member 5 after use can be restricted and the user can recognize that the administration of liquid is completed.

Further, the cover main body 60 of the cover member 6 and the grasping portion 52 of the operation member 5 have a transparent window portion (not depicted) for indicating whether or not administration of liquid is completed. In the unused state (initial state), the projecting pieces 43*a* of the outer tube 4 do not seen but the inner tube 3 is seen through the window portions. Then, if administration of liquid is completed, then the projecting pieces 43*a* are seen through the corresponding window portion. Consequently, the user can recognize that the administration of liquid is completed.

Further, when the operation member 5 moves in the direction toward the distal end, the projections 67 of the rotor 65 are attached to the inclined faces 5141 of the projecting pieces 514 to rotate the rotor 65 clockwise as viewed in plan of the pusher 51. When the rotor 65 rotates, the projections 67 of the rotor 65 move to the proximal side of the staircases 524 of the operation member 5 by a predetermined number of stages in response to the amount of rotation of the rotor 65. Then, after the administration of liquid, the projections 67 of the rotor 65 move to the proximal side of the grooves 526.

In this manner, at the steps [3] and [4], since movement of the operation member 5 is permitted after completion of rotation of the outer tube 4, the inclined faces 5141 of the projecting pieces 514 of the operation member 5 and the projections 67 of the rotor 65 are brought into contact with each other and rotation of the rotor 65 is started. Therefore, rotation of the rotor 65 can be prevented with certainty before administration of drug solution. Further, drug solution can be administrated with resistance reduced by continuous rotation of the outer tube 4 and the rotor 65.

Figure 25:
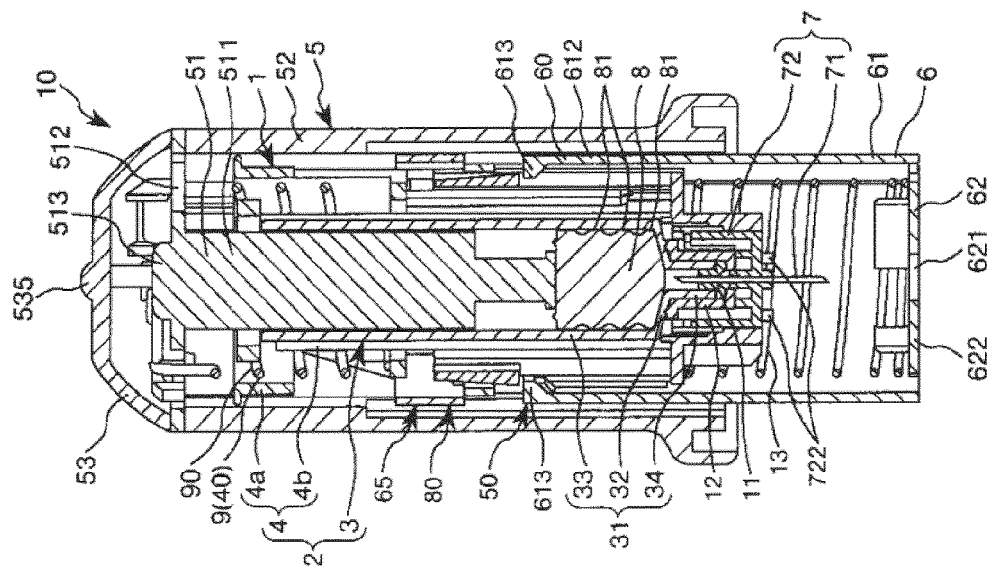
FIG. 25 is a vertical sectional view depicting operational state in order upon use of the liquid administration tool depicted in FIG. 1.
Figure 27:
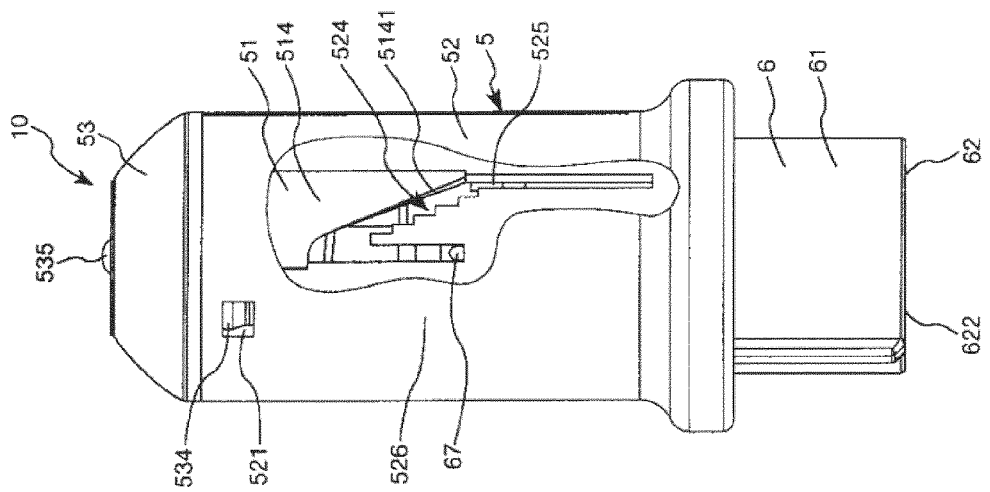
FIG. 27 is a lateral view depicting operational state in order upon use of the liquid administration tool depicted in FIG. 1.
Figure 26:
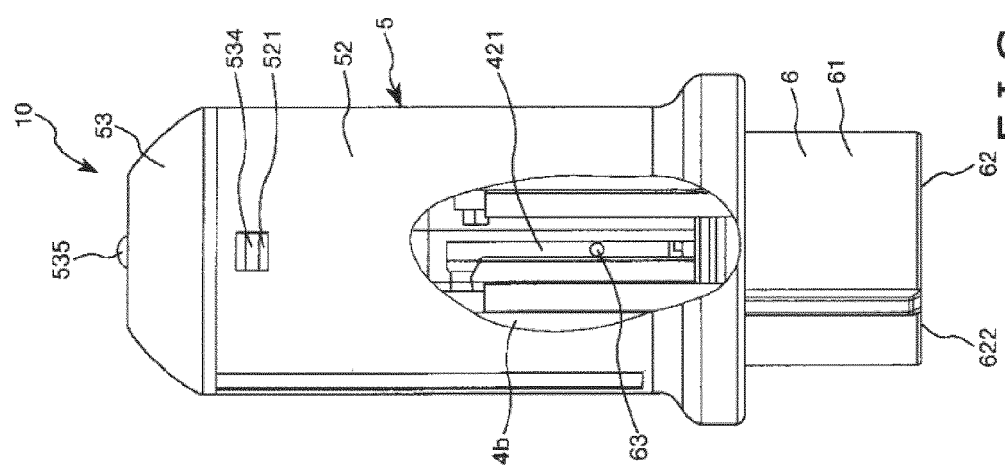
FIG. 26 is a lateral view depicting operational state in order upon use of the liquid administration tool depicted in FIG. 1.

[5] Then, pressing of the operation member 5 in the direction toward the distal end is stopped, and the distal wall portion 62 of the cover member 6 is separated from the living body and the double-ended needle 71 is pulled out from the living body as depicted in FIGS. 25 to 27.

Consequently, the cover member 6 is moved in the direction toward the distal end, namely, moved to the fifth position (position (A)), and the distal side needle tip of the double-ended needle 71 is covered with the cover member 6.

Along with this, when the projections 67 move in the direction toward the distal end of the grooves 526 until the movement amount of the cover member 6 in the direction toward the distal end of the cover member 6 reaches the lock permitting movement amount, the projections 67 attach to distal portions (attaching portions) 5261 of the grooves 526 thereby to restrict the position of the cover member 6 in the direction toward the distal end with respect to the operation member 5. In other words, the movement of the cover member 6 in the direction toward the distal end is blocked. Consequently, the cover member 6 is prevented from being separated from the grasping portion 52.

Further, the movement of the cover member 6 to the position (B) is restricted by the locking unit 50. In particular, the projections 613 of the cover member 6 are engaged with the proximal end of the elongated holes 44*b* to block the cover member 6 from moving in the direction toward the proximal end with respect to the outer tube 4. As a result, the state in which the distal side needle tip of the double-ended needle 71 is covered with the cover member 6 is maintained. Consequently, since the cover member 6 cannot move in the direction toward the proximal end, it functions as a safety unit for preventing a needle piercing accident after use.

Further, when the outer tube 4 rotates relative to the cover member 6, the projections 613 of the cover member 6 are engaged with the elongated holes 44*b* from the grooves 43*b* of the outer tube 4 (initial state) and the safety unit functions. Therefore, the liquid administration tool 10 is less likely to return to the initial state than that of the straight type, and the states before and after use are easy to recognize. Therefore, the liquid administration tool 10 can be prevented from being used again. Further, the liquid administration tool 10 after used can be discarded with certainty without being mistaken as a liquid administration tool 10 before use.

Further, when the cover member 6 is positioned at the fifth position through the movement of the projections 63 of the cover member 6 in the direction toward the distal end relative to the cover member 6 along the linear grooves 423, the projections 63 of the cover member 6 are positioned at a position depicted in FIG. 26 with respect to the outer tube 4.

[6] Here, upon administration of liquid, before the pressing operation is completed, for example, pain by liquid or puncture pain by the double-ended needle 71 sometimes occurs, by which it is obliged to pull out the double-ended needle 71 once from the living body to interrupt the administration of liquid.

In this case, it is stopped to press the operation member 5 in the direction toward the distal end (pressing of the cover main body 60 against the surface of the living body is cancelled). Then, the distal wall portion 62 of the cover member 6 is separated from the living body and the double-ended needle 71 is pulled out from the living body.

Consequently, the cover member 6 tends to move in the direction toward the distal end by the biasing force of the coil spring 13. However, in the state in which the projections 613 of the cover member 6 are positioned on the proximal side with respect to the elongated holes 44*b* of the outer tube 4, the projections 67 of the cover member 6 attach to a predetermined stage of the staircases 524 of the operation member 5 to restrict movement of the cover member 6 in the direction toward the distal end (refer to FIGS. 28 and 29).

Figure 29:
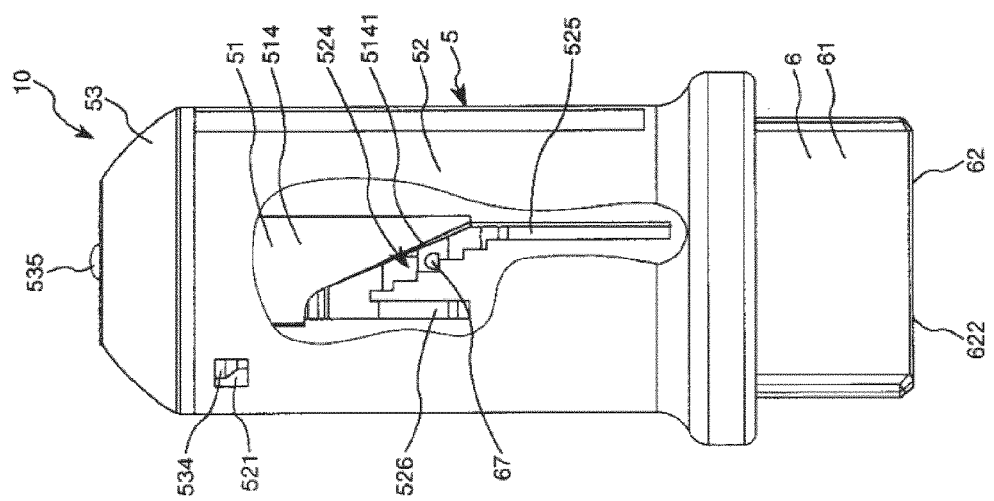
FIG. 29 is a lateral view depicting operational state in order upon use of the liquid administration tool depicted in FIG. 1.

Note that, thereupon, also it is possible to set the cover member 6 so as to move by a predetermined distance before the projections 67 of the cover member 6 are attached to the predetermined stage of the staircases 524 of the operation member 5, and also it is possible to set the cover member 6 so as not to move at all. Further, as described hereinabove, also it is possible to set the cover member 6 such that, in the state in which the projections 67 of the cover member 6 attach to the predetermined stage of the staircases 524 of the operation member 5, the distal side needle tip of the double-ended needle 71 is exposed from the distal end of the cover member 6 as depicted in FIG. 29, and also it is possible to set the cover member 6 such that the distal side needle tip is not exposed as depicted in FIG. 28.

In this manner, since the projections 67 attach to a predetermined stage of the staircases 524, the amount of movement of the cover member 6 when the cover member 6 moves in the direction toward the distal end by the biasing force of the coil spring 13 is restricted so as not to reach the lock permitting movement amount. Consequently, restriction of the movement of the cover member 6 to the position (B) by the locking unit 50 is not performed.

When administration of liquid is to be re-started, the distal wall portion 62 of the cover member 6 is attached to the living body and the operation member 5 is pressed in the direction toward the distal end. Along with this, the cover member 6 can move to the position (B) and administration of liquid is re-started.

As described above, when administration of liquid is performed, for example, pain by liquid or puncture pain by the double-ended needle 71 sometimes occurs, by which it is obliged to pull out the double-ended needle 71 once from the living body to interrupt the administration of liquid. In this case, the cover member 6 moves in the direction toward the distal end back to the position (A) by the biasing force of the coil spring 13, and if the movement amount of the cover member 6 reaches the lock permitting movement amount, then the movement of the cover member 6 to the position (B) is restricted by the locking unit 50. However, with the present liquid administration tool 10, since the movement amount restriction unit 80 restricts the amount of movement of the cover member 6, establishment of such a situation as just described can be prevented with certainty. Then, after the pain disappears, the double-ended needle 71 can puncture the living body again to re-start the pressing operation.

In this manner, with the liquid administration tool 10, when administration of liquid is performed, even if the administration of liquid is interrupted, the administration can be re-started with certainty before the administration of liquid is completed. Consequently, desired administration of liquid can be performed with certainty.

Further, after the administration of liquid is completed, the cover member 6 returns to the position (A). When the movement amount of the cover member 6 reaches the lock permitting movement amount, movement of the cover member 6 to the position (B) is restricted by the locking unit 50. Consequently, the state in which the distal side needle tip of the double-ended needle 71 is covered with the cover member 6 is maintained, and puncture in error by the distal side needle tip of the double-ended needle 71 after use can be prevented with certainty.

Further, when administration of liquid is performed, the movement of the operation member 5 in the direction toward the distal end can be assisted by the biasing force of the coil spring 9, namely, by the assisting force. Consequently, even in a case in which a comparatively thin double-ended needle is used as the double-ended needle 71 or liquid having comparatively high viscosity is administrated, the liquid can be administrated easily and with certainty. Further, even a user who is difficult to perform a pressing operation for the operation member 5 such as, for example, an old person or a female having weak force or an arthritis patent having pain or deformation in a finger of a hand can administrate liquid easily and with certainty.

Further, since the biasing force of the coil spring 9 is used as the assisting force for a pressing operation, administration of liquid can be performed in accordance with a pace of the user.

Further, the puncture action of the living body by the double-ended needle 71, the rotating action of the outer tube 4, and a pressing operation of the operation member 5 can be performed smoothly as a single continuous action.

Second Embodiment

Figure 30:
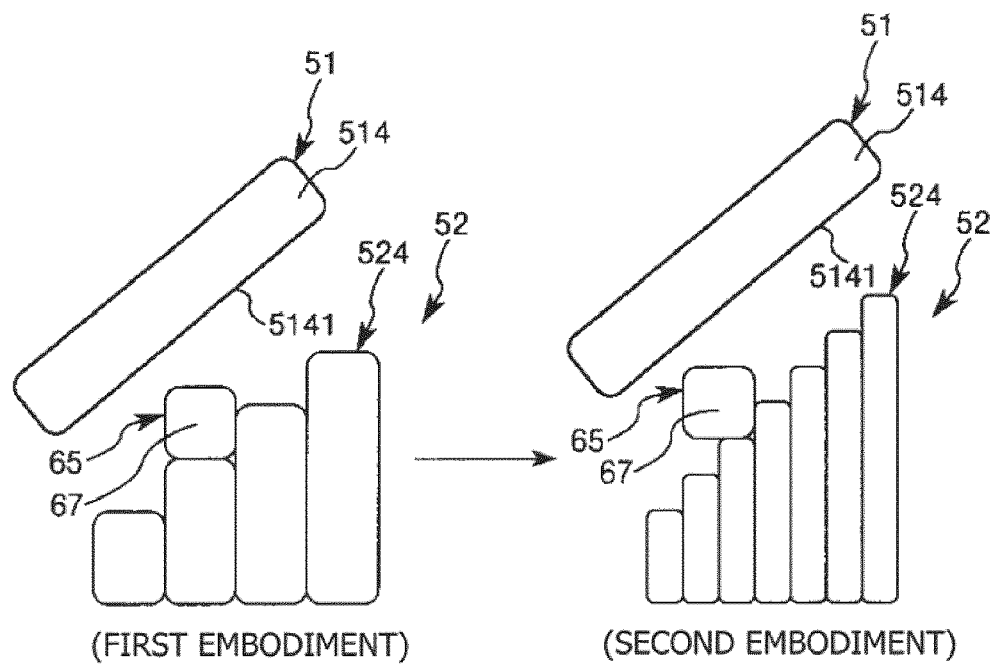
FIG. 30 is a view schematically depicting principal part in a second embodiment of a liquid administration tool of the present disclosure.

FIG. 30 is a view schematically depicting principal part of a second embodiment of a liquid administration tool of the present disclosure.

In the following, the second embodiment is described principally in regard to differences thereof from the aforementioned first embodiment while description of like matters are omitted herein to avoid redundancy.

As depicted in FIG. 30, in the liquid administration tool 10 of the second embodiment, the distance between the stages of the staircases 524 of the movement amount restriction unit 80 is set smaller than that in the first embodiment. Consequently, when administration of liquid is interrupted, the accuracy in movement amount of the cover member 6 restricted by the movement amount restriction unit 80 can be increased.

With the liquid administration tool 10 described, effects similar to those of the aforementioned first embodiment can be achieved.

Note that the second embodiment can be applied also to a third, a fifth, and a sixth embodiments described below.

Third Embodiment

Figure 31:
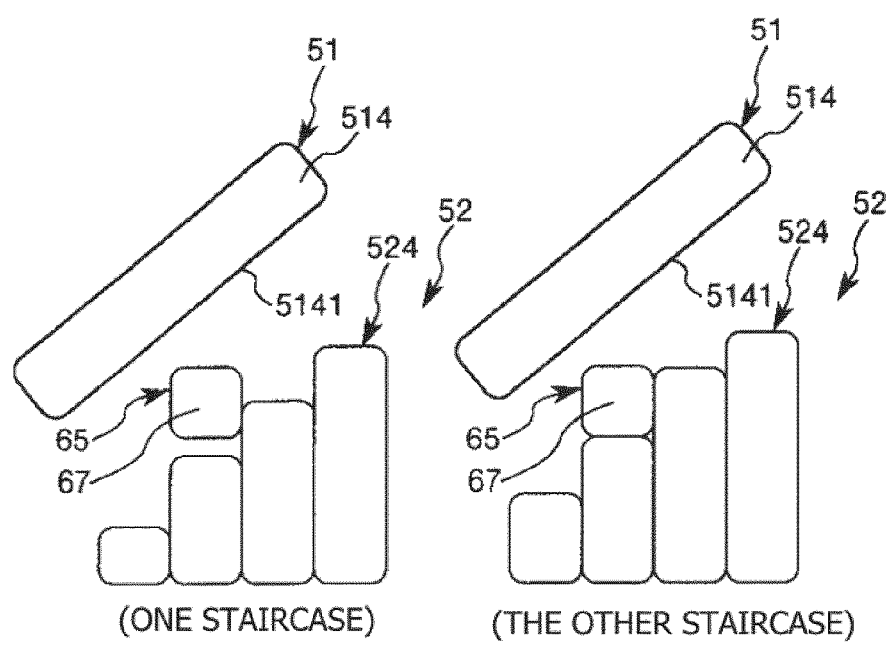
FIG. 31 is a view schematically depicting principal part in a third embodiment of a liquid administration tool of the present disclosure.

FIG. 31 is a view schematically depicting principal part in a third embodiment of a liquid administration tool of the present disclosure.

In the following, the third embodiment is described principally in regard to differences thereof from the aforementioned first embodiment while description of like matters are omitted herein to avoid redundancy.

As depicted in FIG. 31, the liquid administration tool 10 of the third embodiment is configured such that the heights of the corresponding stages of one and the other of the pair of staircases 524 of the movement amount restriction unit 80 (distances in the axial direction from the proximal end of the operation member 5) are set different from each other such that the height of each stage alternately increases between the one staircase 524 and the other staircase 524. Further, the projections 67 of the rotor 65 are configured for engagement alternately with the one staircase 524 and the other staircase 524. Consequently, when administration of liquid is interrupted, the accuracy in movement amount of the cover member 6 restricted by the movement amount restriction unit 80 can be increased.

With the liquid administration tool 10 described, effects similar to those of the aforementioned first embodiment can be achieved.

Note that the third embodiment can be applied also to the fifth and the sixth embodiments hereinafter described.

Fourth Embodiment

Figure 32:
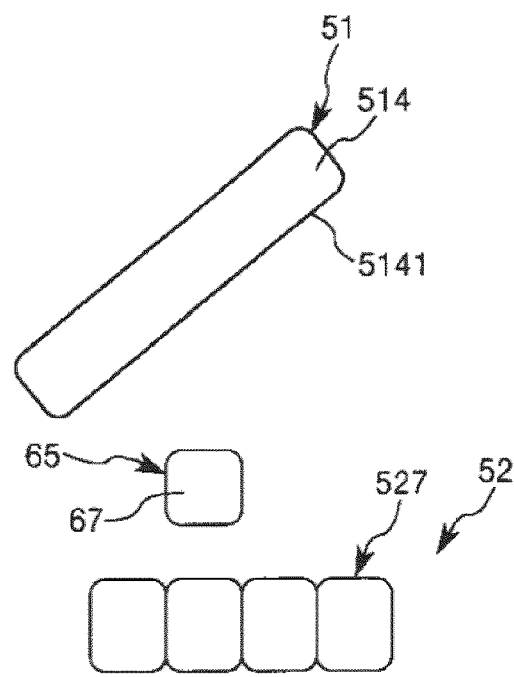
FIG. 32 is a view schematically depicting principal part in a fourth embodiment of a liquid administration tool of the present disclosure.

FIG. 32 is a view schematically depicting principal part in a fourth embodiment of a liquid administration tool of the present disclosure.

In the following, the fourth embodiment is described principally in regard to differences thereof from the aforementioned first embodiment while description of like matters are omitted herein to avoid redundancy.

As depicted in FIG. 32, in the liquid administration tool 10 of the fourth embodiment, the movement amount restriction unit 80 has a flattened portion (engaging portion) 527 in place of the staircase 524. This flattened portion 527 is set such that, in a state in which the projection 67 of the rotor 65 attaches to (engages with) the flattened portion 527, the projection 613 of the cover member 6 is positioned on the proximal side with respect to the elongated holes 44b of the outer tube 4.

With the liquid administration tool 10 described, effects similar to those of the aforementioned first embodiment can be achieved.

Note that the fourth embodiment can be applied also to the fifth and the sixth embodiments.

Fifth Embodiment

Figure 33:
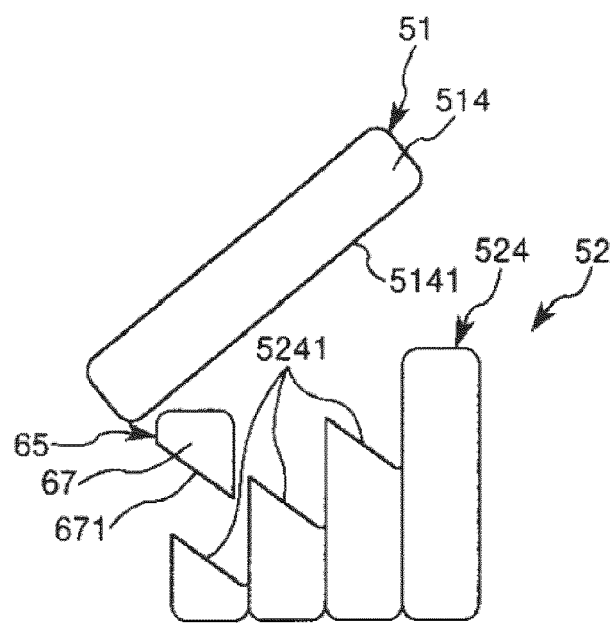
FIG. 33 is a view schematically depicting principal part in a fifth embodiment of a liquid administration tool of the present disclosure.

FIG. 33 is a view schematically depicting principal part in a fifth embodiment of a liquid administration tool of the present disclosure.

In the following, the fifth embodiment is described principally in regard to differences thereof from the aforementioned first embodiment while description of like matters are omitted herein to avoid redundancy.

As depicted in FIG. 33, in the liquid administration tool 10 of the fifth embodiment, each of the stages of the staircase 524 of the movement amount restriction unit 80 and the projection 67 of the rotor 65 have an inclined face 5241 and an inclined face 671, respectively, which engage with each other. Consequently, when administration of liquid is interrupted, the state in which the stages of the staircase 524 and the projection 67 engage with each other can be maintained with certainty, and movement of the cover member 6 in the direction toward the distal end can be blocked with certainty.

With the liquid administration tool 10 described, effects similar to those of the aforementioned first embodiment can be achieved.

Note that the fifth embodiment can be applied also to the sixth embodiment.

Sixth Embodiment

Figure 34:
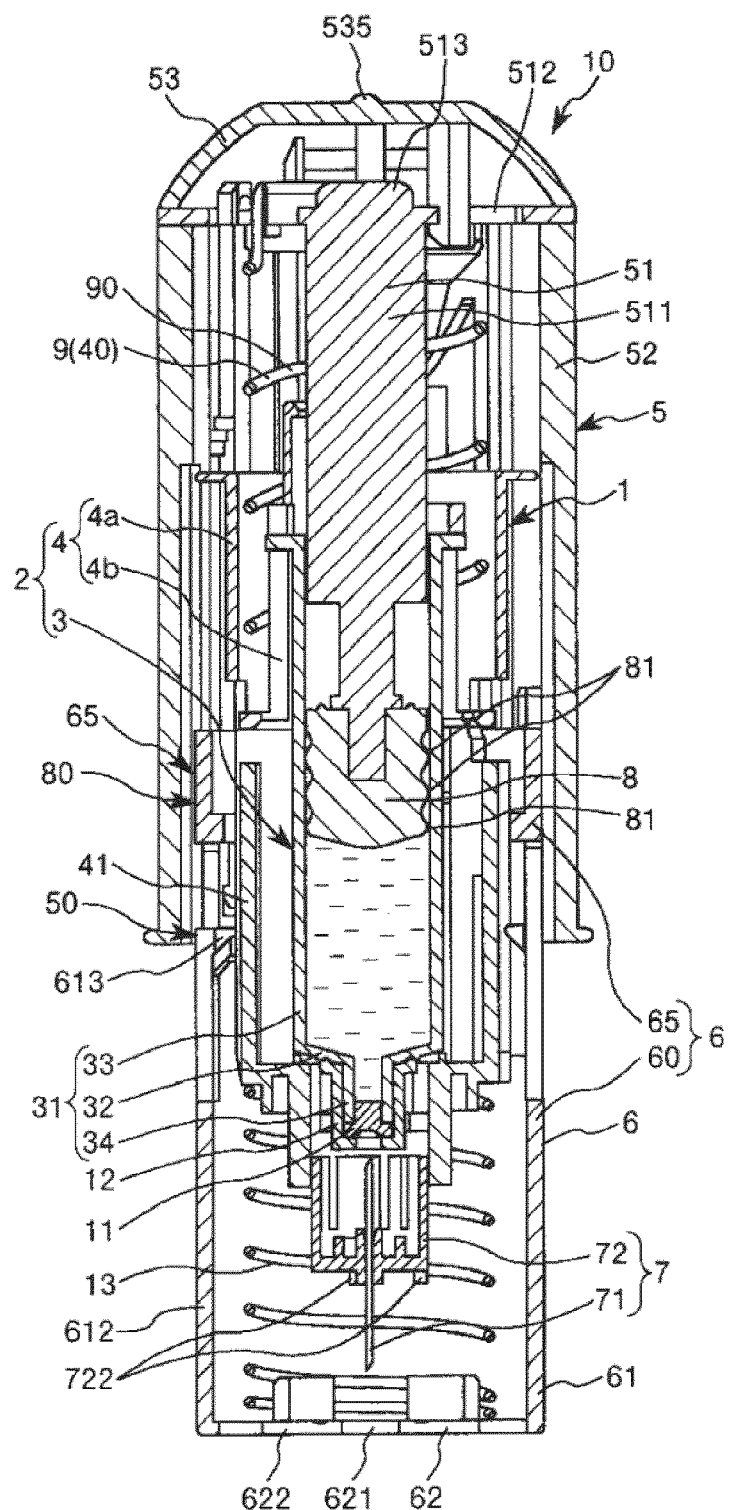
FIG. 34 is a vertical sectional view depicting a sixth embodiment of a liquid administration tool of the present disclosure.
Figure 35:
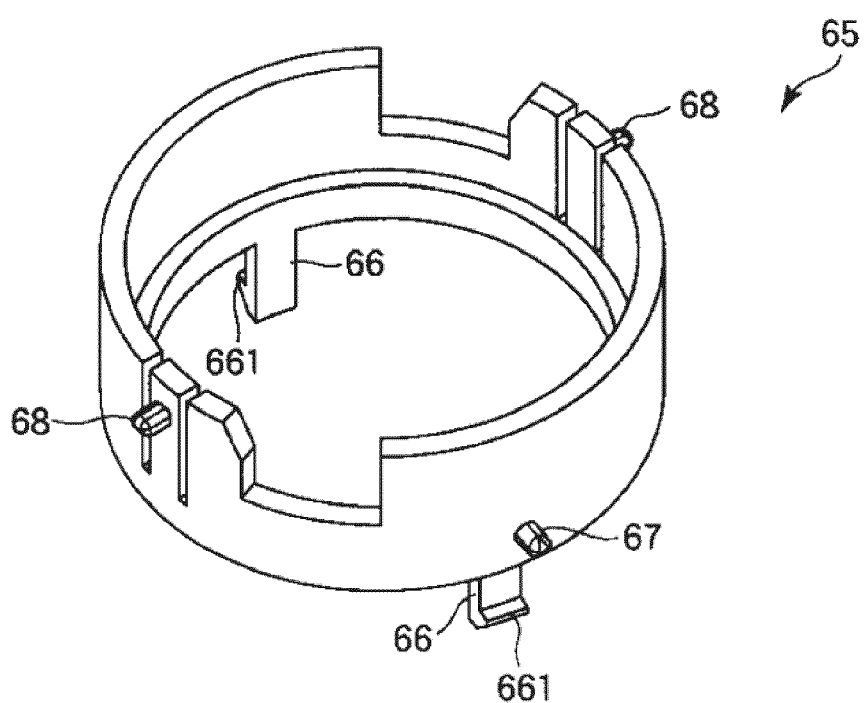
FIG. 35 is a perspective view of a rotor of a cover member of the liquid administration tool depicted in FIG. 34.
Figure 36:
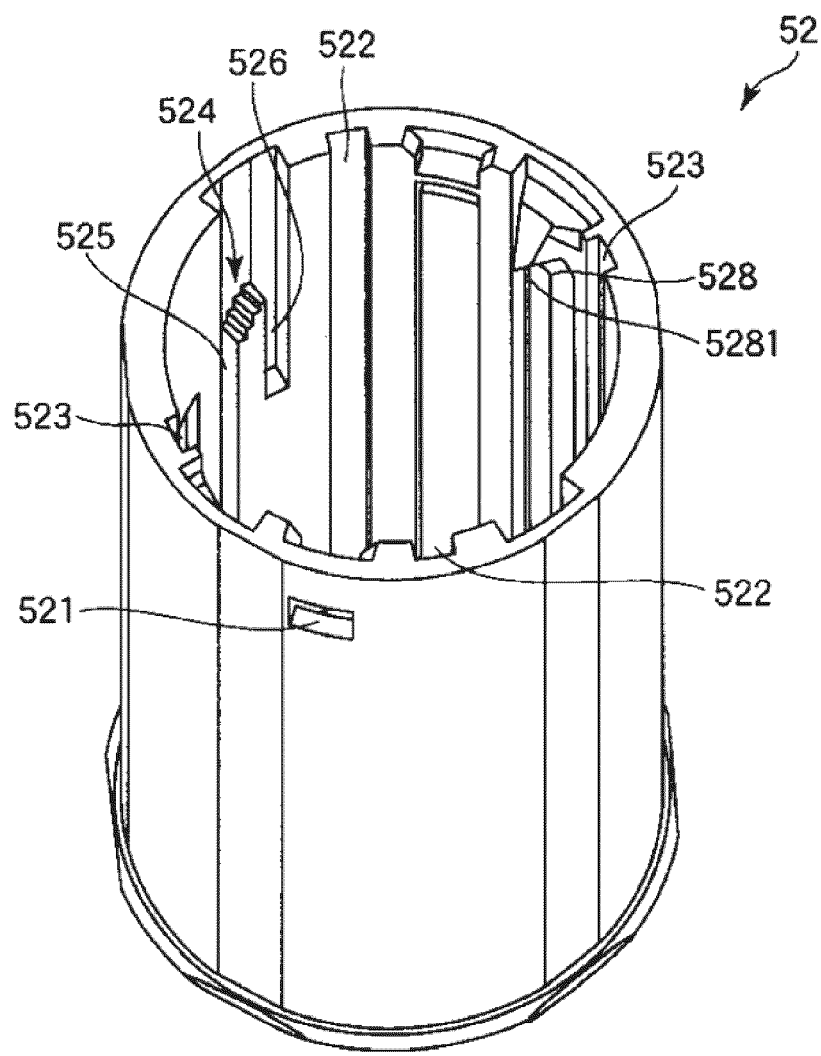
FIG. 36 is a perspective view of a grasping portion of an operation portion of the liquid administration tool depicted in FIG. 34.
Figure 37:
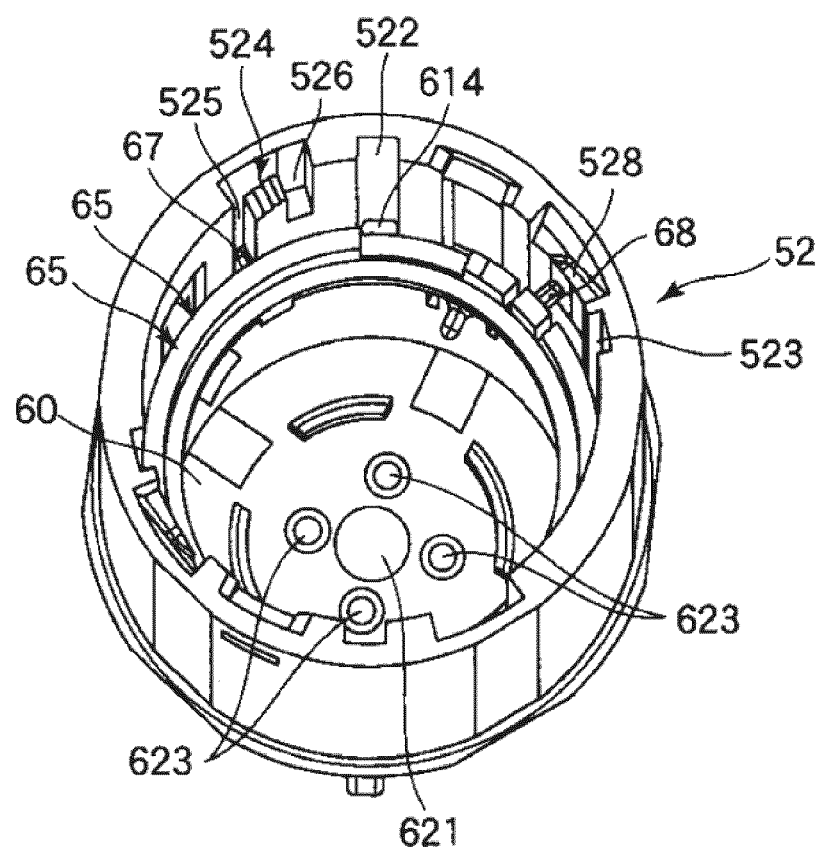
FIG. 37 is a perspective view of the cover member and the grasping portion of the operation portion of the liquid administration tool depicted in FIG. 34.

FIG. 34 is a vertical sectional view depicting a sixth embodiment of a liquid administration tool of the present disclosure. FIG. 35 is a perspective view of a rotor of a cover member of the liquid administration tool depicted in FIG. 34. FIG. 36 is a perspective view of a grasping portion of an operation portion of the liquid administration tool depicted in FIG. 34. FIG. 37 is a perspective view of the cover member and the grasping portion of the operation portion of the liquid administration tool depicted in FIG. 34.

In the following, the sixth embodiment is described principally in regard to differences thereof from the aforementioned first embodiment while description of like matters are omitted herein to avoid redundancy.

As depicted in FIGS. 34 to 37, in the liquid administration tool 10 of the sixth embodiment, the movement amount restriction unit 80 has a pair of projections (first protrusions) 67 and another pair of projections (second protrusions) 68 provided on the rotor 65, and a pair of staircases 524 and a pair of roofs 528 provided on the grasping portion 52 of the operation member 5.

The pair of projections 68 are formed on an outer circumferential face of the rotor 65 such that they project to the outer side and oppose to each other.

Meanwhile, the pair of roofs 528 are formed on an inner circumferential face of the grasping portion 52 such that they are opposed to each other. Further, the face of each of the roofs 528 on the distal side forms an inclined face (attachment face) 5281 which is inclined along a circumferential direction of the grasping portion 52. Upon a pressing operation, the projections 68 of the rotor 65 attach to the inclined faces 5281 of the roofs 528 to rotate the rotor 65 clockwise as viewed in plan. In this manner, the inclined faces 5281 of the roofs 528 have a function of attaching, upon a pressing operation, to the projections 68 to rotate the rotor 65, namely, a function similar to that of the projecting pieces 514 of the pusher 51 in the first embodiment.

With the liquid administration tool 10 described, effects similar to those of the aforementioned first embodiment can be achieved.

Seventh Embodiment

Figure 38:
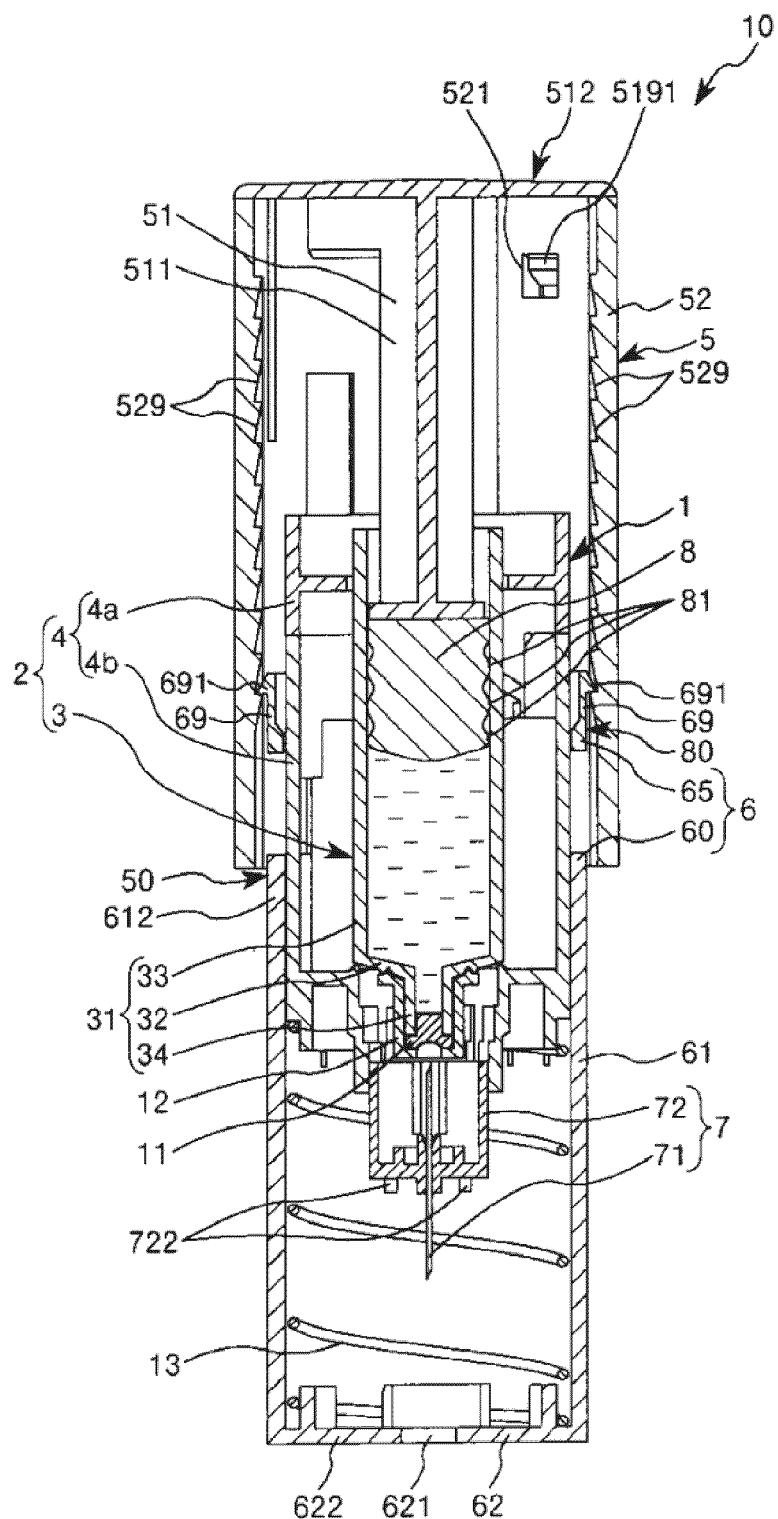
FIG. 38 is a vertical sectional view depicting a seventh embodiment of a liquid administration tool of the present disclosure.
Figure 39:
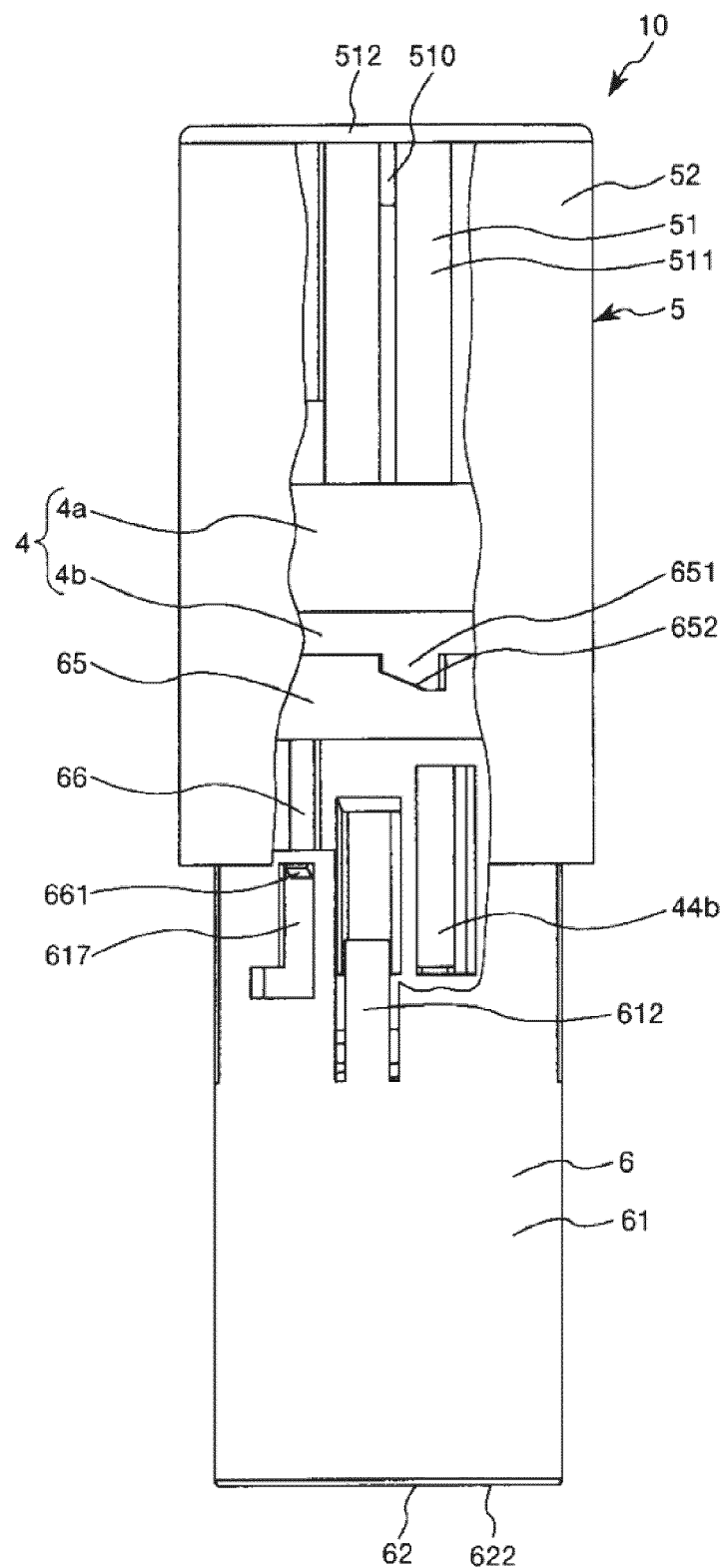
FIG. 39 is a lateral view of the liquid administration tool depicted in FIG. 38.
Figure 41:
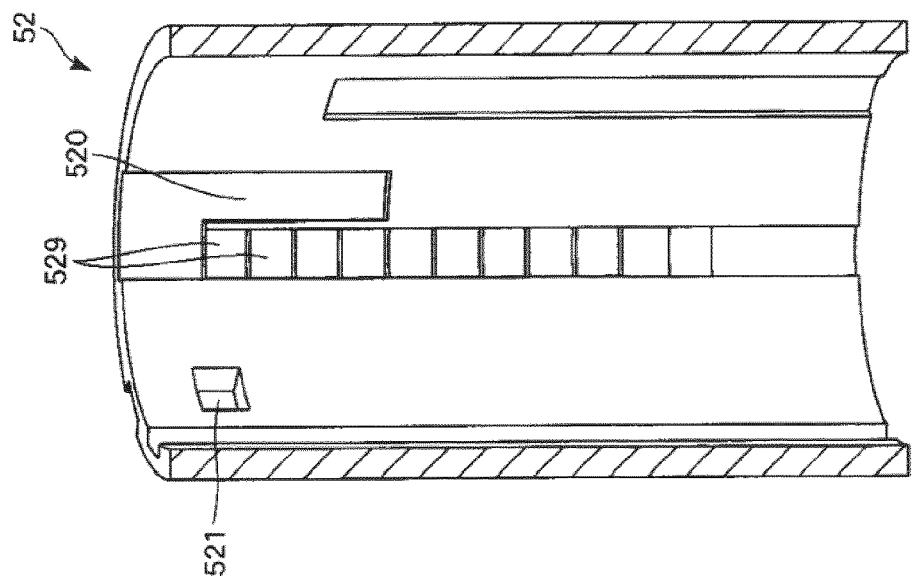
FIG. 41 is a sectional perspective view of a grasping portion of the operation member of the liquid administration tool depicted in FIG. 38.
Figure 40:
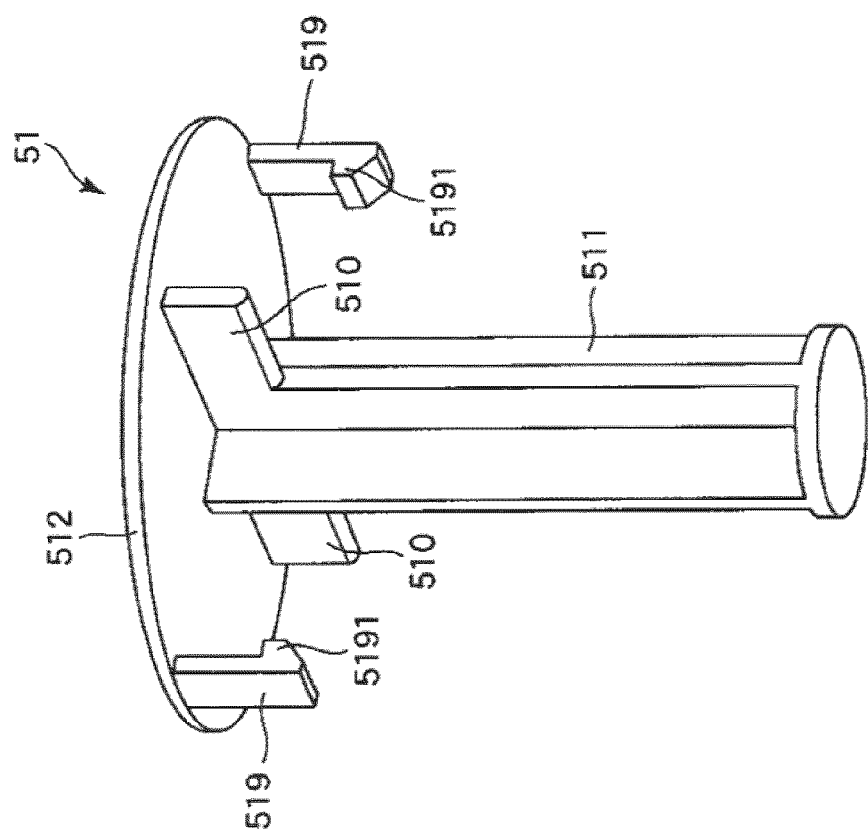
FIG. 40 is a perspective view of a pusher of an operation member of the liquid administration tool depicted in FIG. 38.
Figure 42:
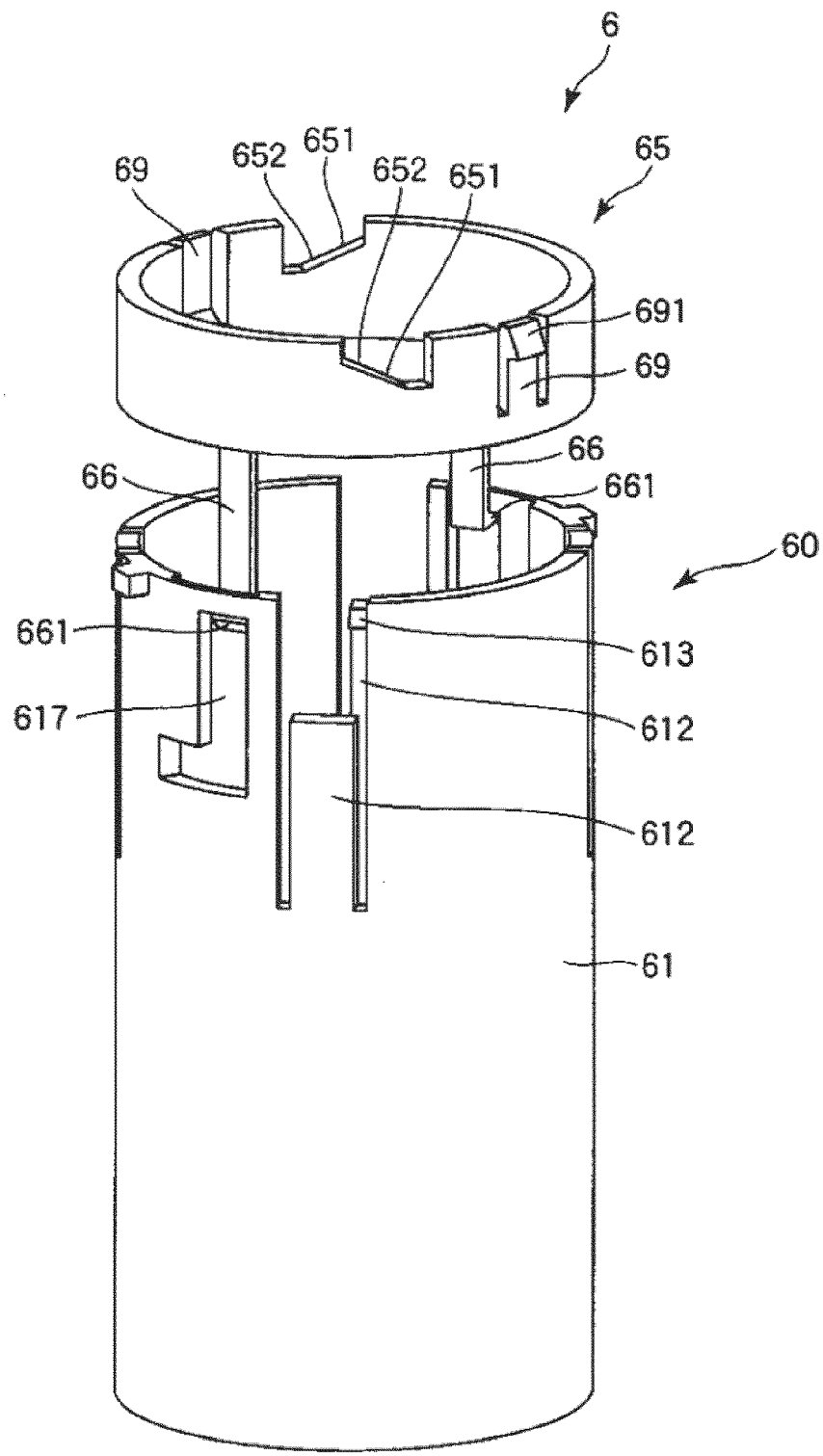
FIG. 42 is a perspective view of a cover member of the liquid administration tool depicted in FIG. 38.

FIG. 38 is a vertical sectional view depicting a seventh embodiment of a liquid administration tool of the present disclosure. FIG. 39 is a lateral view of the liquid administration tool depicted in FIG. 38. FIG. 40 is a perspective view of a pusher of an operation member of the liquid administration tool depicted in FIG. 38. FIG. 41 is a sectional perspective view of a grasping portion of the operation member of the liquid administration tool depicted in FIG. 38. FIG. 42 is a perspective view of a cover member of the liquid administration tool depicted in FIG. 38. FIGS. 43 to 50 depict operational states in order upon use of the liquid administration tool depicted in FIG. 38, and wherein FIGS. 43, 45, 47, and 49 are vertical sectional views and FIGS. 44, 46, 48, and 50 are lateral views.

In the following, the seventh embodiment is described principally in regard to differences thereof from the aforementioned first embodiment while description of like matters are omitted herein to avoid redundancy.

The liquid administration tool 10 of the seventh embodiment depicted in FIGS. 38 to 42 is configured such that, when administration of liquid is interrupted, the distal side needle tip of the double-ended needle 71 is not exposed from the distal end of the cover member 6.

As depicted in FIG. 40, a pair of arm portions 519 having elasticity are formed on the distal side of the flange 512 of the pusher 51 of the operation member 5 such that they are disposed in an opposing relationship to each other and project in the direction toward the distal end. A pawl 5191 is formed at a distal portion of each of the arm portions 519 such that it projects toward the inner side. The pawls 5191 of the arm portions 519 are inserted in and engaged with the hole portions 521 of the grasping portion 52 to interlock the pusher 51 and the grasping portion 52 to each other.

Further, a pair of ribs 510 are formed on the distal side of the flange 512 of the pusher 51 such that they are disposed in an opposing relationship to each other and project in the direction toward the distal end.

Further, as depicted in FIG. 41, a plurality of recessed portions (engaging portions) 529 are formed along an axial direction of the grasping portion 52 on an inner circumferential face of the grasping portion 52. A pair of recessed portion groups each configured from the plurality of recessed portions 529 are formed in an opposing relationship to each other. Further, a pair of grooves 520 are formed on an inner circumferential face of the grasping portion 52 such that they are opposed to each other. The grooves 520 have an L shape and extend in an axial direction and a peripheral direction of the grasping portion 52.

Further, as depicted in FIG. 42, a pair of elongated holes 617 are formed at a proximal portion of the side wall 61 of the cover main body 60 of the cover member 6 such that they are disposed in an opposing relationship to each other. The elongated holes 617 have an L shape and extend in the axial direction and the circumferential direction of the side wall 61.

Further, a pair of arm portions 66 having elasticity are formed on the distal side of the rotor 65 such that they are disposed in an opposing relationship to each other and project in the direction toward the distal end. Further, a pawl 661 is formed at a distal portion of each of the arm portions 66 such that it projects toward the outer side. The pawls 661 are inserted in and engaged with the elongated holes 617 from the inner side of the proximal side of the cover main body 60 to interlock the rotor 65 and the cover main body 60 to each other. The pawls 661 can individually move in the axial direction and the circumferential direction of the cover main body 60 along the elongated holes 617. Consequently, the rotor 65 can move in the axial direction of the cover main body 60 relative to the cover main body 60 and can relatively rotate around the center axis of the cover main body 60.

Further, a pair of arm portions 69 having elasticity are formed on the rotor 65 such that they are disposed in an opposing relationship to each other and project in the direction toward the proximal end. A pawl (protrusion) 691 is formed at a distal portion of each of the arm portions 69 such that it projects toward the outer side. The pawls 691 are individually engageable with the plurality of recessed portions 529 or grooves 520 of the cover member 6.

Further, a pair of cutout portions 651 are formed on the proximal side of the rotor 65 such that they are disposed in an opposing relationship to each other. The face of each of the cutout portions 651 on the proximal side forms an inclined face (attachment face) 652 which is inclined along the circumferential direction of the rotor 65. Upon a pressing operation, immediately before the pressing operation is completed, the ribs 510 of the pusher 51 are attached to the inclined faces 652 of the cutout portions 651 to rotate the rotor 65 clockwise as viewed in plan.

Now, a method of use of the liquid administration tool 10 and operation states of the liquid administration tool 10 during use are described with reference to FIGS. 38, 39, and 43 to 50.

[1] A liquid administration tool 10 in an unused state is prepared as depicted in FIGS. 38 and 39. In the liquid administration tool 10 in the unused state, the pawls 691 of the rotor 65 engage with the recessed portions 529 on the distal side from among the plurality of recessed portions 529 of the grasping portion 52.

Figure 44:
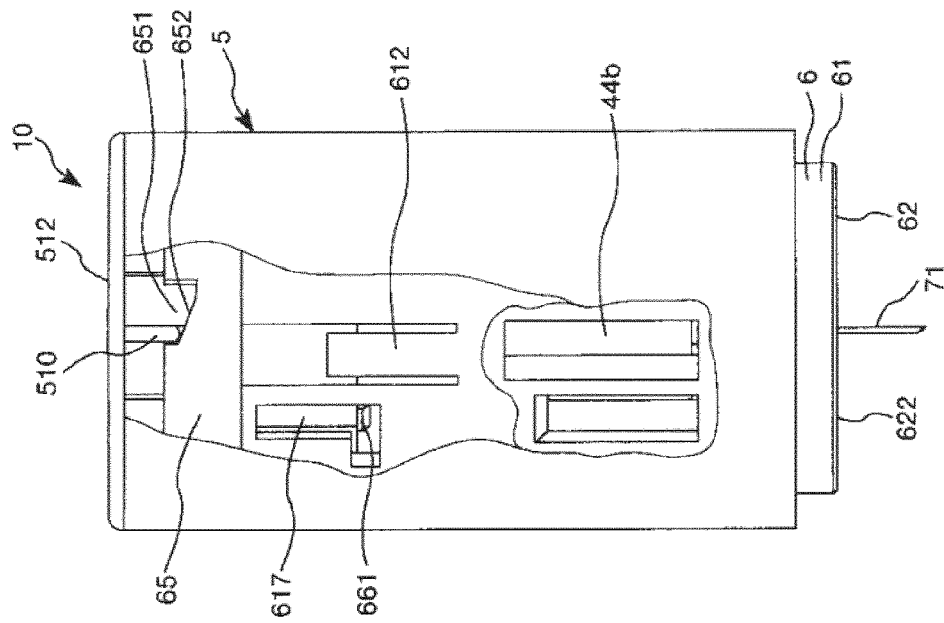
FIG. 44 is a lateral view depicting operational state in order upon use of the liquid administration tool depicted in FIG. 38.
Figure 43:
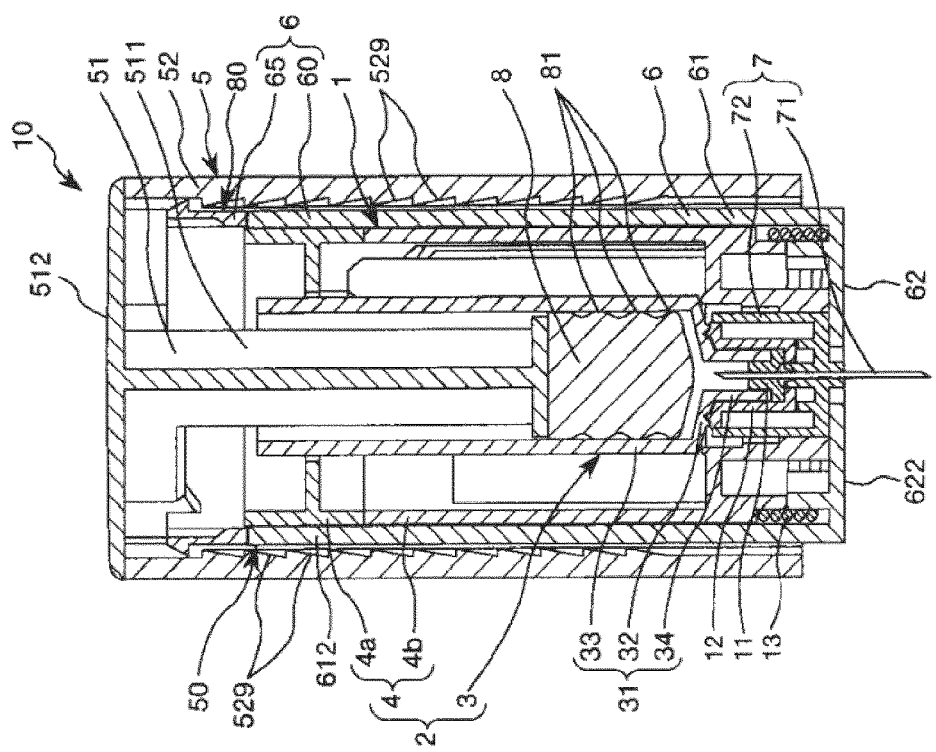
FIG. 43 is a vertical sectional view depicting operational state in order upon use of the liquid administration tool depicted in FIG. 38.

[2] As depicted in FIGS. 43 and 44, during administration of liquid, the pawls 691 of the rotor 65 move in the direction toward the proximal end along the plurality of recessed portions 529 of the grasping portion 52.

Further, immediately before the pressing operation (administration of liquid) is completed, the ribs 510 of the pusher 51 are attached to the inclined faces 652 of the cutout portions 651 to rotate the rotor 65 clockwise as viewed in plan. Along with this, the pawls 661 of the rotor 65 move the distal portions of the elongated holes 617 in a circumferential direction of the cover main body 60 (refer to FIG. 46).

Figure 46:
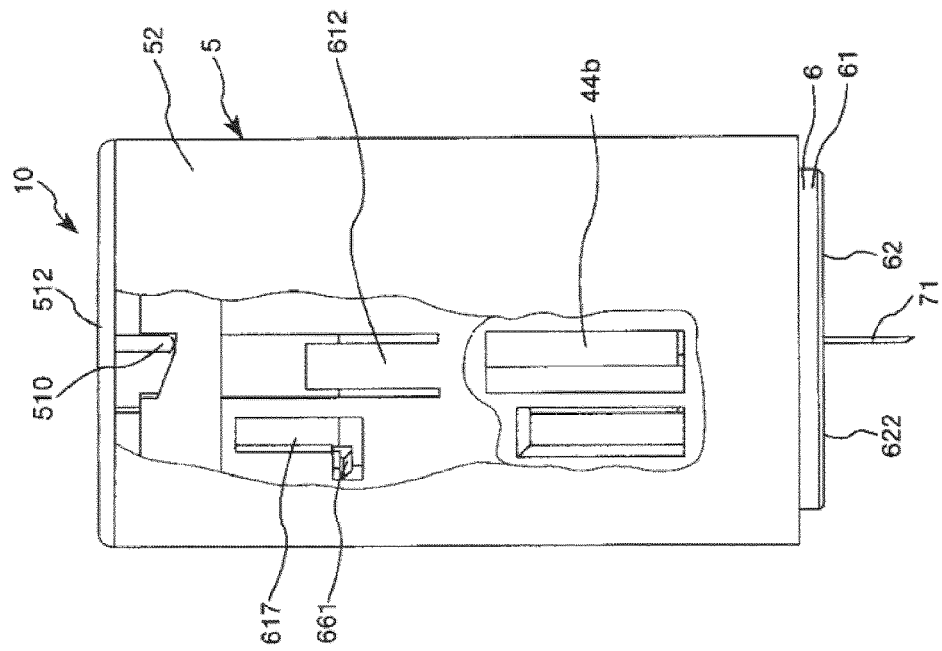
FIG. 46 is a lateral view depicting operational state in order upon use of the liquid administration tool depicted in FIG. 38.
Figure 45:
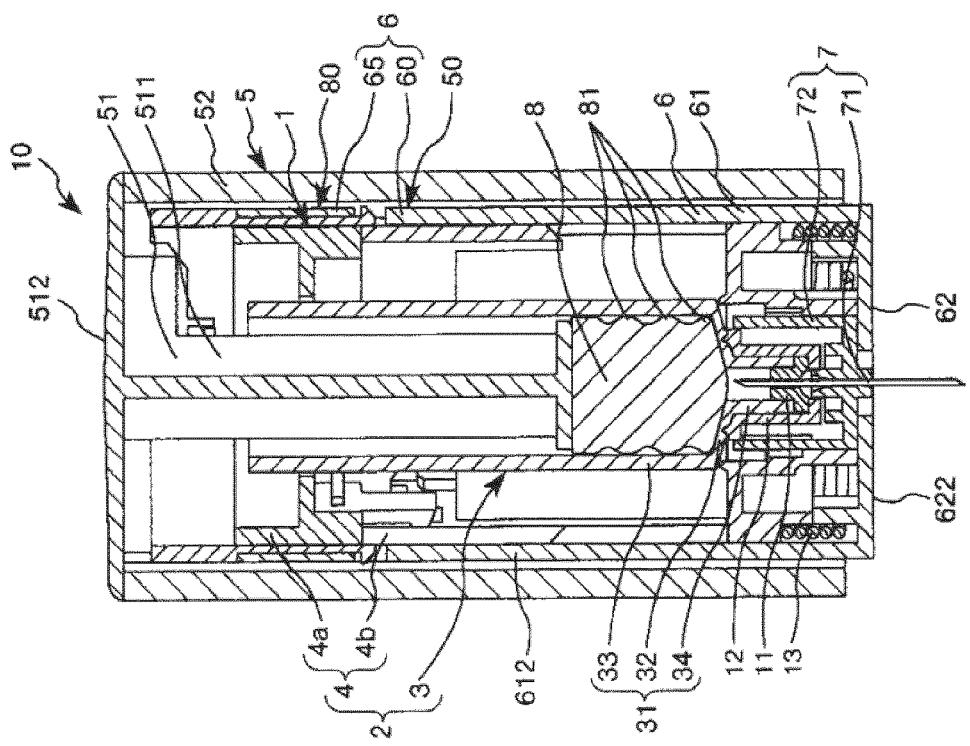
FIG. 45 is a vertical sectional view depicting operational state in order upon use of the liquid administration tool depicted in FIG. 38.

[3] As depicted in FIGS. 45 and 46, after the administration of liquid is completed, the pawls 661 of the rotor 65 are engaged with the distal portions of the elongated holes 617. Consequently, movement of the rotor 65 in the axial direction with respect to the cover main body 60 is blocked, and the rotor 65 and the cover main body 60 are permitted to move integrally with each other in the axial direction.

Further, the pawls 691 of the rotor 65 are positioned at a location on the right side in FIG. 41 of the grooves 520 of the cover main body 60, namely, at a location at which the plurality of recessed portions 529 do not exist.

Figure 48:
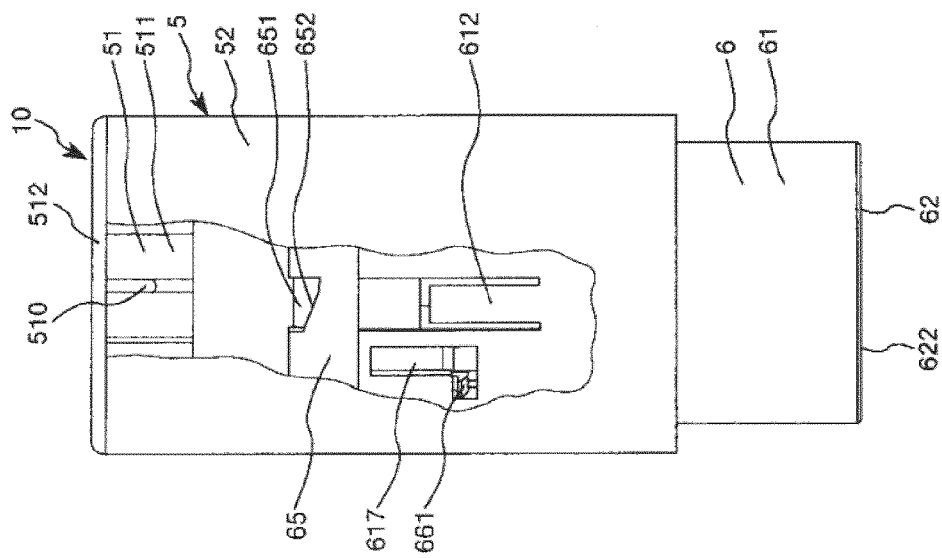
FIG. 48 is a lateral view depicting operational state in order upon use of the liquid administration tool depicted in FIG. 38.
Figure 47:
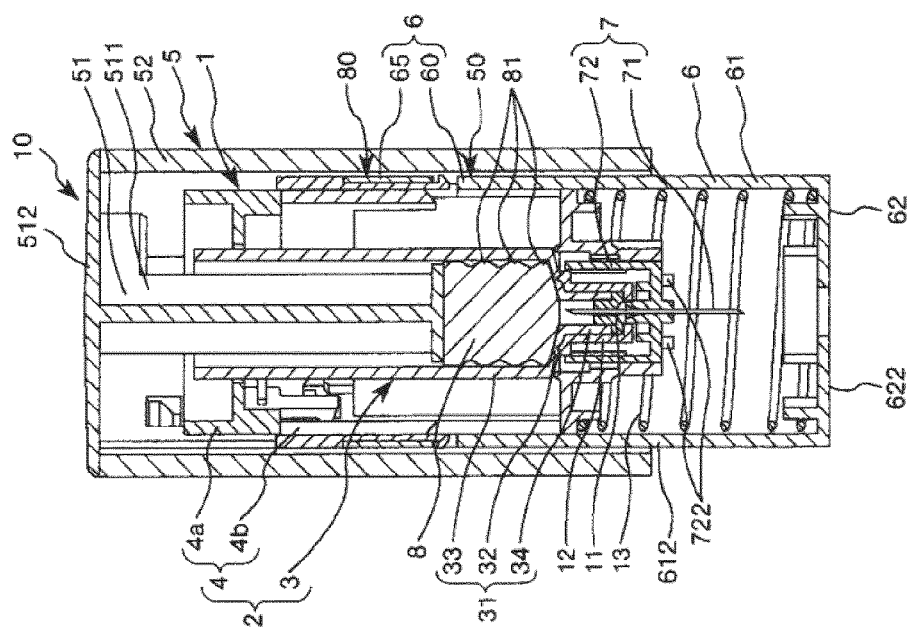
FIG. 47 is a vertical sectional view depicting operational state in order upon use of the liquid administration tool depicted in FIG. 38.

[4] Then, the pressing of the operation member 5 in the direction toward the distal end is stopped, and the distal wall portion 62 of the cover member 6 is separated from the living body and the double-ended needle 71 is pulled out from the living body as depicted in FIGS. 47 and 48.

Consequently, the cover member 6 is moved in the direction toward the distal end, namely, to the position (A), by the biasing force of the coil spring 13, whereupon the distal side needle tip of the double-ended needle 71 is covered with the cover member 6.

Further, thereupon, the pawls 691 of the rotor 65 move in the direction toward the distal end along the grooves 520 of the cover main body 60, and when the amount of movement of the cover member 6 in the direction toward the distal end reaches the lock permitting movement amount, the pawls 691 are attached to the distal portions (attachment portions) of the grooves 520 thereby to restrict the position of the cover member 6 in the direction toward the distal end with respect to the operation member 5. In other words, movement of the cover member 6 in the direction toward the distal end is blocked. Consequently, the cover member 6 is prevented from being separated from the grasping portion 52.

Further, the movement of the cover member 6 to the position (B) is restricted by the locking unit 50.

[5] Here, when administration of liquid is performed, before the pressing operation is completed, for example, pain by the liquid or puncture pain by the double-ended needle 71 sometimes occurs, by which it is obliged to pull out the double-ended needle 71 once from the living body to interrupt the administration of liquid.

In this case, the pressing of the operation member 5 in the direction toward the distal end is stopped (pressing of the cover main body 60 against the surface of the living body is cancelled), and the distal wall portion 62 of the cover member 6 is separated from the living body and the double-ended needle 71 is pulled out from the living body.

Figure 50:
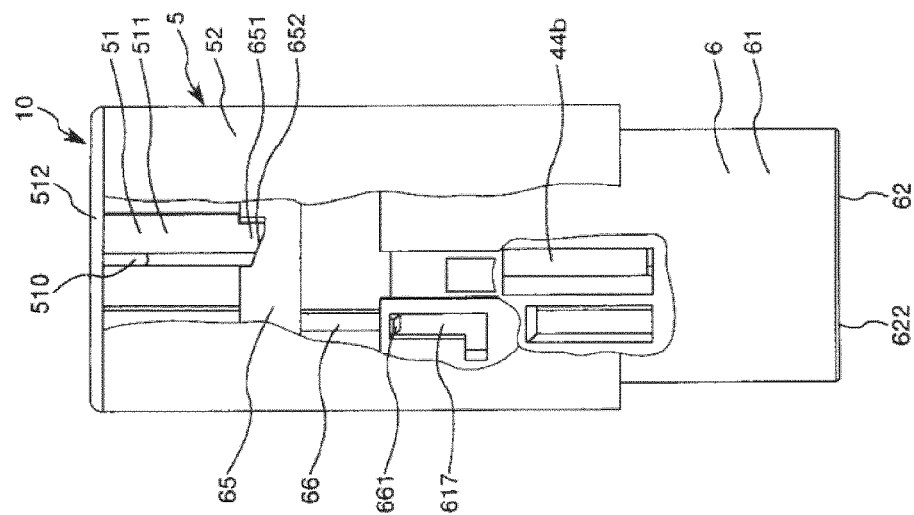
FIG. 50 is a lateral view depicting operational state in order upon use of the liquid administration tool depicted in FIG. 38.
Figure 49:
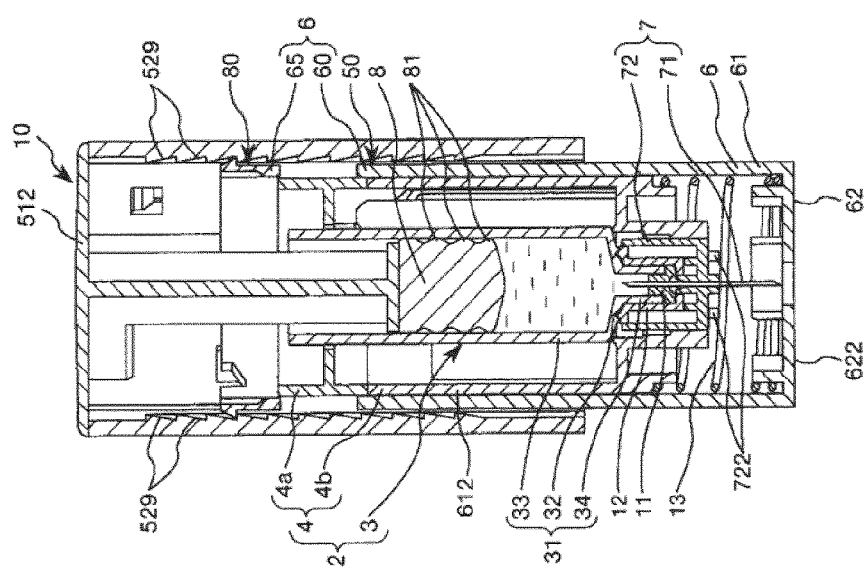
FIG. 49 is a vertical sectional view depicting operational state in order upon use of the liquid administration tool depicted in FIG. 38.

Consequently, the cover member 6 is moved in the direction toward the distal end by the biasing force of the coil spring 13 as depicted in FIGS. 49 and 50. In this case, the rotor 65 is blocked from moving in the direction toward the distal end through engagement of the pawls 691 thereof with predetermined ones of the plurality of recessed portions 529 of the grasping portion 52. On the other hand, although the cover main body 60 moves in the direction toward the distal end, in the state in which the projections 613 of the cover member 6 are positioned on the proximal side with respect to the elongated holes 44*b* of the outer tube 4, the pawls 661 of the rotor 65 are engaged with proximal portions of the elongated holes 617 of the cover main body 60 to block movement of the cover main body 60 in the direction toward the distal end.

Note that, in the state in which the pawls 661 are engaged with the proximal portions of the elongated holes 617, the distal side needle tip of the double-ended needle 71 is not exposed from the distal end of the cover member 6.

In this manner, the amount of movement of the cover member 6 is restricted by the movement amount restriction unit 80 so that the movement amount when the cover member 6 is moved in the direction toward the distal end by the biasing force of the coil spring 13 does not reach the lock permitting movement amount. Consequently, restriction of the movement of the cover member 6 to the position (B) by the locking unit 50 is not performed.

When administration of liquid is to be re-started, the distal wall portion 62 of the cover member 6 is attached to the living body and the operation member 5 is pressed in the direction toward the distal end. Along with this, the cover member 6 can move to the position (B), and administration of liquid is re-started.

With the liquid administration tool 10 described, effects similar to those of the aforementioned first embodiment can be achieved.

Although the liquid administration tool of the present disclosure has been described in connection with the embodiments depicted in the drawings, the present disclosure is not limited to them, and the configurations of the components can be replaced by arbitrary configurations of similar functions. Further, some other arbitrary components may be added to the present disclosure.

Further, the present disclosure may be a combination of two or more arbitrary ones of the configurations (features) of the embodiments described hereinabove.

Further, while, in the embodiments described hereinabove, the puncture needle has a needle tube in the form of a double-ended needle, the present disclosure is not limited to this, and the puncture needle may have a needle tube whose needle tip on the proximal side is omitted. In this case, the needle tube is fitted in the inner tube in advance (already in the unused state).

Further, while, in the embodiments described hereinabove, liquid is filled in the tubular body in advance, the present disclosure is not limited to this. For example, liquid may not initially be filled in the tubular body, and the liquid administration tool may be used after liquid is filled into the tubular body later.

Further, while, in the embodiments described hereinabove, the coil spring 13 serving as a biasing member is a compression spring, the present disclosure is not limited to this, and for example, a tension spring or the like may be used or a biasing member other than a spring may be used.

Further, while, in the embodiments described hereinabove, the coil spring 9 serving as a biasing member is a tension spring, the present disclosure is not limited to this, and for example, a compression spring or the like may be used or a biasing member other than a spring may be used.

Further, while, in the embodiments described hereinabove, the biasing force of the coil spring 9 serving as a biasing member is used as assisting force for a pressing operation, the present disclosure is not limited to this, and the liquid administration tool may be configured such that administration of liquid is performed automatically by the biasing force of the coil spring 9. Alternatively, the coil spring 9 may be omitted.

Further, while the tubular body in the inside of which the gasket slidably moves in the embodiments described above is configured from two members of the inner tube and the outer tube, the present disclosure is not limited to this, and the tubular body may be configured, for example, from a single member.

Further, in the present disclosure, the gasket may be omitted. In this case, the liquid administration tool is configured such that the distal portion of the pusher functions as a gasket.

The liquid administration tool of the present disclosure includes a structure including a tubular body which has a bottom portion at a distal portion and an opening portion at a proximal portion and in which liquid can be filled and a needle tube which is positioned at a distal portion of the tubular body and has an incisive needle tip at a distal end thereof, the needle tube being communicatable at a proximal end thereof with the inside of the tubular body, an operation member having a pusher and configured to perform a pressing operation of moving the pusher in a direction toward the distal end to discharge the liquid from the needle tube, a cover member movable between a position (A) at which the cover member covers at least the needle tip of the needle tube and another position (B) at which the cover member is retracted in a direction toward the proximal end from the position (A) and the needle tip is exposed, a biasing member configured to bias the cover member in the direction toward the distal end, a locking unit configured to restrict, when the cover member is moved from the position (B) to the position (A) by biasing force of the biasing member and a movement amount of the cover member reaches a lock permitting movement amount, the movement of the cover member to the position (B), and a movement amount restriction unit configured to restrict the movement amount of the cover member such that the movement amount when the cover member is moved in the direction toward the distal end by the biasing force of the biasing member does not reach the lock permitting movement amount until the cover member is positioned at the position (B) and the pressing operation is completed.

When administration of liquid is performed, for example, pain by the liquid or puncture pain by a needle tube sometimes occurs, by which it is obliged to pull out the needle tube once from the living body to interrupt the administration of liquid. In this case, the cover member moves in the direction toward the distal end back to the position (A) by the biasing force of the biasing member, and if the movement amount of the cover member reaches the lock permitting movement amount, then the movement of the cover member to the position (B) is restricted by the locking unit. However, since the movement amount restriction unit restricts the amount of movement of the cover member, establishment of such a situation as just described can be prevented with certainty. Then, after the pain disappears, the needle tube can puncture the living body again to re-start the pressing operation.

In this manner, with the liquid administration tool of the present disclosure, when administration of liquid is performed, even if the administration of liquid is interrupted, the administration can be re-started with certainty before the administration of liquid is completed. Consequently, desired administration of liquid can be performed with certainty.

Further, after the administration of liquid is completed, the movement of the cover member to the position (B) is restricted by the locking unit. Consequently, the state in which the needle tip of the needle tube is covered with the cover member is maintained, and as a result, puncture in error by the needle tip of the needle tube after use can be prevented with certainty. Accordingly, the liquid administration tool of the present disclosure has industrial applicability.

It should be understood by those skilled in the art that various modifications, combinations, sub-combinations and alterations may occur depending on design requirements and other factors insofar as they are within the scope of the appended claims or the equivalents thereof.

What is claimed is:

1. A liquid administration tool comprising:
    a structure comprising:
        a tubular body in which liquid is fillable, the tubular body having a bottom portion at a distal end and, an opening portion at a proximal end, and
        a needle tube positioned at a distal portion of the tubular body, the needle tube having a needle tip at a distal end thereof, and the needle tube being communicable at a proximal end thereof with an inside of the tubular body;
    an operation member having a pusher and configured to perform a pressing operation of moving the pusher in a distal direction to discharge the liquid from the needle tube;
    a cover member movable between (i) a predetermined first position at which the cover member covers at least the needle tip of the needle tube, and (ii) a predetermined second position at which the cover member is proximally retracted from the first position and the needle tip is exposed, wherein the cover member includes:
        a cover main body having a tubular shape, and
        a rotor provided on the cover main body for relative rotation around a center axis of the cover main body and configured to rotate during the pressing operation, in an interlocking relationship with the cover main body;
    a biasing member configured to bias the cover member in the distal direction;
    a locking unit configured to restrict the movement of the cover member to the second position when (i) the cover member is moved from the second position to the first position by biasing force of the biasing member, and (ii) a movement amount of the cover member reaches a lock permitting movement amount; and
    a movement amount restriction unit configured to restrict the movement amount of the cover member such that, when the cover member is moved in the direction toward the distal end by the biasing force of the biasing member, the movement amount cannot reach the lock permitting movement amount unless the cover member has first reached the second position.

2. The liquid administration tool according to claim 1, wherein the movement amount restriction unit includes:
    a projection provided on the rotor; and
    an engaging portion provided on the operation member and engageable with the projection.

3. The liquid administration tool according to claim 2, wherein:
    the operation member has a grasping portion having a cylindrical shape and set to an outer periphery side of the structure and the rotor, the operation member being configured to be grasped upon use of the liquid administration tool, and
    the engaging portion is provided on an inner circumferential face of the grasping portion.

4. The liquid administration tool according to claim 2, wherein the movement amount restriction unit has an attachment face provided on the operation member and configured to attach to the projection upon the pressing operation to rotate the rotor.

5. The liquid administration tool according to claim 4, wherein the attachment face is provided on the pusher.

6. The liquid administration tool according to claim 2, wherein:
    the operation member has an attachment portion configured to attach to the projection if the movement amount of the cover member reaches the lock permitting movement amount, and
    when the movement amount of the cover member reaches the lock permitting movement amount, distal movement of the cover member with respect to the operation member is restricted by attachment of the projection to the attachment portion.

7. The liquid administration tool according to claim 1, wherein the liquid is drug solution.

* * * * *